US009696285B2

United States Patent
Duraffourg et al.

(10) Patent No.: US 9,696,285 B2
(45) Date of Patent: Jul. 4, 2017

(54) GAS ANALYSIS SYSTEM COMPRISING A GAS SPECTROMETER EQUIPPED WITH A MICRO-REFLECTRON

(71) Applicants: Commissariat a L'Energie Atomique et aux Energies Alternatives, Paris (FR); Analytical Pixels Technology-Apix Technology, Grenoble (FR)

(72) Inventors: Laurent Duraffourg, Voiron (FR); Philippe Andreucci, Moirans (FR); Charles-Marie Tassetti, Paris (FR); Eric Colinet, Bois Guillaume (FR); Pierre Puget, Saint Ismier (FR); Joshua Whiting, Springboro, OH (US); Peter Thomas Stevens, Springboro, OH (US); Mélanie Petitjean, Grenoble (FR)

(73) Assignees: COMMISSARIAT A L'ENERGIE ATOMIQUE ET AUX ENERGIES ALTERNATIVES (FR); Analytical Pixels Technology-Apix Technology (FR)

( * ) Notice: Subject to any disclaimer, the term of this patent is extended or adjusted under 35 U.S.C. 154(b) by 0 days.

(21) Appl. No.: 14/419,108

(22) PCT Filed: Aug. 5, 2013

(86) PCT No.: PCT/EP2013/066345
§ 371 (c)(1),
(2) Date: Feb. 2, 2015

(87) PCT Pub. No.: WO2014/020177
PCT Pub. Date: Feb. 6, 2014

(65) Prior Publication Data
US 2015/0204827 A1    Jul. 23, 2015

(30) Foreign Application Priority Data

Aug. 3, 2012 (FR) ..................................... 12 57606

(51) Int. Cl.
*H01J 49/00* (2006.01)
*G01N 30/72* (2006.01)
(Continued)

(52) U.S. Cl.
CPC ...... *G01N 30/7206* (2013.01); *H01J 49/0018* (2013.01); *H01J 49/405* (2013.01); *G01N 2030/025* (2013.01)

(58) Field of Classification Search
None
See application file for complete search history.

(56) References Cited

U.S. PATENT DOCUMENTS 7,098,449 B1 * 8/2006 Miller ................. H01J 49/0018
250/281
8,552,367 B2 * 10/2013 Danel ................. H01J 49/0018
250/287
(Continued)

FOREIGN PATENT DOCUMENTS

EP          2211185 A1      7/2010
FR    EP 2211185 A1 *      7/2010 ......... G01C 19/5656
(Continued)

OTHER PUBLICATIONS

E. Wapelhorst, J.P. Hauschild, J. Müller, 'Complex MEMS: a fully integrated TOF micro mass spectrometer', Sensors and Actuators A 138 (2007) 22-27.
(Continued)

*Primary Examiner* — Andrew Smyth
(74) *Attorney, Agent, or Firm* — Lerner, David, Littenberg, Krumholz & Mentlik, LLP

(57) ABSTRACT

The invention relates to a gas analysis system comprising, from upstream to downstream:

a module (SEP) for separating at least a portion of the species contained in the gas to be analysed, comprising at least one microcapillary column (GC) for gas phase chromatography, and a time-of-flight mass spectrometer (TOFMS) coupled to said separation module, said spectrometer comprising a ion source (MS1, MS2) adapted to ionise at least a portion of said species and to emit a ion beam, and a free-flight zone (MS4) for said ions, said mass spectrometer (TOFMS) being arranged in the volume of at least one substrate and comprising a microreflectron (R) arranged between the source (MS1, MS2) and the free-flight zone (MS4), a wall (R1) of said microreflectron comprising a layer made from a resistive material designed to be polarised between at least two regions so as to create a continuous electrostatic field gradient in said reflectron.

20 Claims, 19 Drawing Sheets

(51) Int. Cl.
  *H01J 49/40* (2006.01)
  *G01N 30/02* (2006.01)

(56) References Cited

U.S. PATENT DOCUMENTS

| | | | | |
|---|---|---|---|---|
| 2008/0087841 A1* | 4/2008 | Verbeck | ............ | H01J 49/0018 250/396 R |
| 2012/0199736 A1* | 8/2012 | Danel | ................ | H01J 49/0018 250/287 |
| 2012/0217389 A1* | 8/2012 | Zheng | .................. | H01J 49/165 250/288 |

FOREIGN PATENT DOCUMENTS

| | | | | |
|---|---|---|---|---|
| FR | EP 2211185 B1 * | 3/2014 | ......... | G01C 19/5656 |
| WO | 2009048739 A2 | 4/2009 | | |
| WO | WO 2009048739 A2 * | 4/2009 | ............ | H01J 49/105 |
| WO | WO 2009048739 A3 * | 11/2009 | ............ | H01J 49/105 |
| WO | 2011154362 A1 | 12/2011 | | |
| WO | WO 2011154362 A1 * | 12/2011 | ............. | G01N 30/60 |

OTHER PUBLICATIONS

P. Siebert, G. Petzold, A. Hellenbart, J. Müller, 'Surface microstructure/miniature mass spectrometer', Applied Physics, A67, 155-160 (1998).

H.J. Yoon, J.H. Kim, E. S. Choi, S. S. Yang, K. W. Jung, 'Fabrication of a novel micro time-of-flight mass spectrometer', Sensors and Actuators A 97-98 (2002) 441-447.

J.P. Hauschild, E. Wapelhorst, J. Muller, 'Mass spectra measured by a fully integrated MEMS mass spectrometer', International Journal of Mass Spectrometry 264 (2007) 53-60.

C. Lu, E. Zellers, Anal. Chem. 2001, 73, 3449.

C. Lu, E. Zellers, Analyst 2002, 127, 1061.

J.M. Sanchez, R.D. Sacks, Anal. Chem. 2003, 75, 978.

J.M. Sanchez, R.D. Sacks, Anal. Chem. 2003, 75, 2231.

J.J. Whiting, C.S. Fix, J.M. Anderson, A. W. Staton, R.P. Manginell, D.R. Wheeler, E.B. Myers, M.L. Roukes, R.J. Simonson, 'High-speed two-dimensional gas chromatography using microfabricated GC columns combined with nanoelectromechanical mass sensors', Transducers 2009, 1666-1669.

E. Mile, G. Jourdan, I. Bargatin, S. Labarthe, C. Marcoux, P. Andreucci, S. Hentz, C. Kharrat, E. Colinet and L. Duraffourg, 'In-plane nanoelectromechanical resonators based on silicon nanowire piezoresistive detection', Nanotechnology 21 (2010) 165504.

Cajka T et al, "Gas chromatography-high-resolution time-of-flight mass spectrometry in pesticide residue analysis: advantages and limitations", Journal of chromatography, Elsevier science publishers B.V, NL, vol, 1058, No. 1-2, Nov. 26, 2004, pp. 251-261, XP004638488.

Preliminary Search Report for Application No. FR1257606 dated May 2, 2013.

International Search Report for Application No. PCT/EP2013/066345 dated Sep. 25, 2013.

* cited by examiner

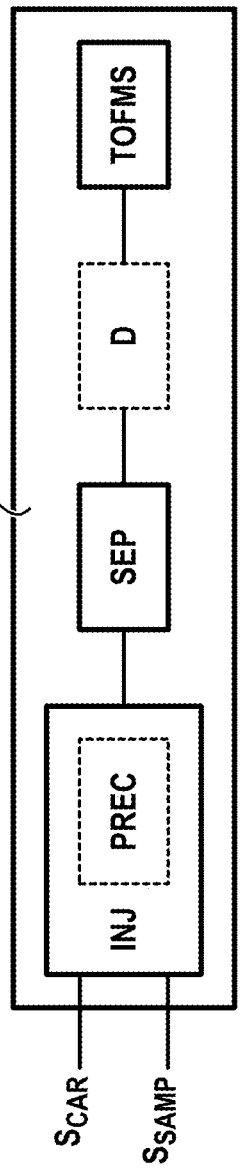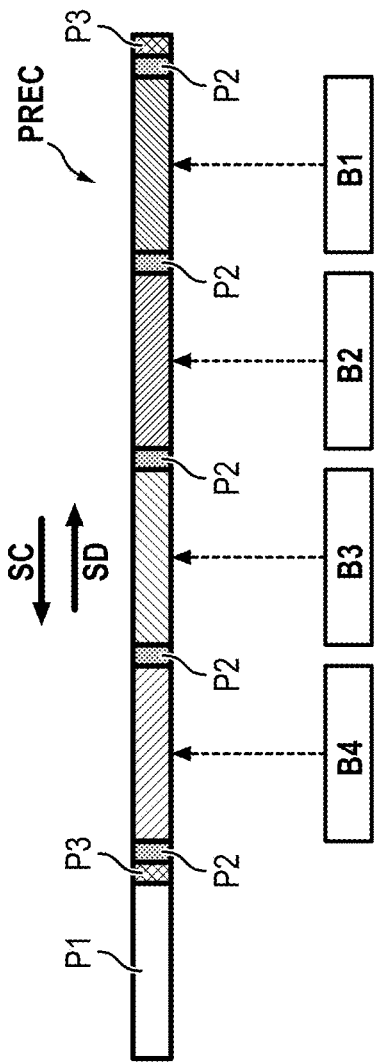

GAS ANALYSIS SYSTEM COMPRISING A GAS SPECTROMETER EQUIPPED WITH A MICRO-REFLECTRON

CROSS REFERENCE TO RELATED APPLICATIONS

The present application is a national phase entry under 35 U.S.C. §371 of International Application No. PCT/EP2013/066345, filed Aug. 5, 2013, published in French, which claims priority from French Patent Application No. 1257606, filed Aug. 3, 2012, the disclosures of which are incorporated by reference herein.

FIELD OF THE INVENTION

This invention relates to a gas analysis system comprising a microcapillary gas phase chromatography column and a time-of-flight mass spectrometer.

BACKGROUND OF THE INVENTION

The time-of-flight mass spectrometry (TOFMS) is very often used for analysing gas [1].

This technique makes it possible to detect the species present in a gas according to their time of travel in a so-called free-flight zone.

To this effect, the gas to be analysed is ionized, which then makes it possible to separate the various species according to their mass to charge ratio, which is usually noted as m/z, where m is the mass of the ion (generally expressed in Daltons (Da)) and z the number of elementary charges.

The ionized species are injected with a certain speed into an electrostatic field.

The forces that are exerted on the ions then modify their trajectory according to the mass to charge ratio of the latter.

The time-of-flight mass spectrometer is based on the measurement of a time of travel that is specific to each species in a so-called free-flight zone, which is a zone devoid of any electrostatic field, wherein the ions move away from one another according to their mass to charge ratio.

The lightest species therefore arrive on a detector placed at the outlet of this free-flight zone before the heaviest species; the mass to charge ratio of each species can then be deduced from the value of the time of flight.

In conventional mass spectrometers, the free-flight zone has a length of about a metre, which imposes a very substantial size, allowing the mass spectrometer to be used only in the laboratory.

For the last ten years or so, various teams have proposed miniaturising these analysis systems in order to make them portable [2] [3].

However, these systems remain either voluminous (as such, "mini" spectrometers have a mass of several kg), or are very little resolved in mass, recalling that the mass resolution of a mass spectrometer refers to the ratio m/Δm, where Δm is the smallest difference in mass that can be measured between two neighbouring peaks, which characterises the ability of the spectrometer to distinguish two peaks corresponding to two species that have a difference in mass Δm.

As such, on miniaturised mass spectrometers, a resolution typically between 10 and 50 on masses between 1 Da and 200 Da is observed, while on commercial time-of-flight mass spectrometers with the highest performance (but which have a size of a few $m^3$), the resolution is from several thousand to 20,000 on ranks of mass from 1 Da to 10,000 Da [2] [4].

A purpose of the invention is therefore to design a gas analysis system that incorporates a time-of-flight mass spectrometer and at least one gas phase chromatography column, having the form of a small-size portable integrated system (with the target mass being less than 1 kg) while still having a reasonable resolution over a wider measurement range than that of the existing miniaturised mass spectrometers.

For the purposes of information, the resolution sought is about from 1000 to 2000 on a rank of mass from 0 to 2000 Da.

BRIEF DESCRIPTION OF THE INVENTION

In accordance with the invention, a gas analysis system is proposed comprising, from upstream to downstream:

a module for separating at least a portion of the species contained in the gas to be analysed, comprising at least one microcapillary gas phase chromatography column, and a time-of-flight mass spectrometer coupled to said separation module, said spectrometer comprising a ion source adapted to ionize at least a portion of said species and to emit a ion beam, and a free-flight zone for said ions, said mass spectrometer being arranged in the volume of at least one substrate and comprising a micro-reflectron arranged between the ion source and the free-flight zone for ions, a wall of said micro-reflectron comprising a layer made from a resistive material designed to be polarised between at least two regions of said layer in such a way as to create a continuous electrostatic field gradient in order to deviate the trajectory of the ions in said micro-reflectron.

In this text, the prefix "micro" designates an element of which at least one of the dimensions is less than 5 mm, more preferably less than 1 mm.

The term "microcapillary" thus relates to a duct, of circular, rectangular or other cross section, of which the diameter of the cross section equivalent to the cross section of a circle is more preferably less than 1 mm.

In this text, the prefix "nano" designates an element of which at least one of the dimensions is less than 1 μm.

In the rest of the text, the term "chromatography", if it is used alone, refers to gas phase chromatography.

According to a preferred embodiment, the micro-reflectron is arranged in such a way as to be passed through by the ions in a longitudinal direction parallel to the direction of the ion beam at the outlet of the source and the resistive layer is designed to be polarised in such a way that the continuous electrostatic field gradient is oriented transversally to the trajectory of the ions in the micro-reflectron.

Advantageously, the micro-reflectron comprises at least two polarising electrodes of the resistive layer, in contact with said at least two regions of the resistive layer, said electrodes extending in the longitudinal direction of the micro-reflectron, in such a way as to generate in said resistive layer a potential gradient in the transverse direction of the micro-reflectron.

The mass spectrometer is arranged in such a way that the trajectory of the ions in the mass spectrometer is included in a channel extending between two planes parallel to a main face of said at least one substrate, with the height of said channel (corresponding to the distance between said planes) being typically less than 1 mm and with the length of said channel being at least ten times greater than said height.

Moreover, said resistive layer of the micro-reflectron extends in a plane parallel to a main face of said at least one substrate.

According to a preferred embodiment, the ion beam is emitted by the source in a direction orthogonal to the direction of introduction, in the spectrometer, of the gas coming from the separation module.

Moreover, the spectrometer comprises, between the ion source and the micro-reflectron, a zone for accelerating ions.

According to an advantageous embodiment, as it is particularly compact, the zone for accelerating ions and the free-flight zone are arranged along a longitudinal wall of the micro-reflectron in such a way as to be adjacent.

As such, more preferably, the micro-reflectron comprises a first opening that communicates with the acceleration zone for the inlet of ions into the reflectron and a second opening that communicates with the free-flight zone for the outlet of the ions, said first and second openings being adjacent in the same wall of the micro-reflectron.

Preferably, the acceleration zone comprises two electrodes extending parallel to the direction of the ion beam emitted by the source, said electrodes being able to be polarised in such a way as to generate an electrostatic field able to deviate the ions in a direction orthogonal to that of the ion beam at the outlet of the source, in order to have said accelerated ions penetrate into the micro-reflectron.

Said electrodes of the acceleration zone are advantageously polarised by a pulse device, in such a way as to have the accelerated ions sequentially enter the micro-reflectron.

The free-flight zone of the spectrometer is generally a separate zone of the micro-reflectron, devoid of any electrostatic field.

Moreover, the substrate in the volume of which said spectrometer is arranged is housed in a sealed case coupled to a vacuum pump in such a way as to apply a vacuum in said case.

According to an embodiment, said at least one microcapillary chromatography column is arranged in the volume of at least one substrate.

According to an embodiment, the separation module comprises at least one non-destructive micro or nano-detector in said at least one microcapillary chromatography column.

According to an embodiment, the separation module comprises at least two microcapillary gas phase chromatography columns coupled in series and each one comprising a different stationary phase, and a flow modulator in order to regulate the flow of gas successively through each one of said columns.

Alternatively, the separation module comprises at least two microcapillary gas phase chromatography columns coupled in series and each one comprising a different stationary phase, each one of said microcapillary columns being arranged in the volume of a substrate and comprising at least two non-destructive micro or nano-detectors arranged in said columns.

According to an advantageous embodiment, the system comprises, upstream of the mass spectrometer, at least one non-destructive micro or nano-detector, said detector being arranged in a duct with a cross section equal to that of a microcapillary chromatography column to which it is connected in such a way as to not modify the cross section of passage of the gas.

According to a particular embodiment, said non-destructive detector is an electromechanical nano-system comprising a resonator and said detector is arranged in the vacuum pressurising case of the mass spectrometer.

Optionally, the system further comprises, upstream of the separation module, a circuit for preconcentrating the gas to be analysed comprising a preconcentrator.

Another object of the invention relates to a method for manufacturing said analysis system.

The manufacturing of the mass spectrometer comprises, in at least one substrate, a step of etching a substrate in order to form at least one portion of a channel for the ions, a step of depositing a resistive layer in a region of said channel intended to form the micro-reflectron, and a step of forming at least two electrodes in order to polarise said resistive layer so as to create a continuous electrostatic field gradient in said reflectron.

The method of manufacturing the spectrometer can further include the cutting of said at least one substrate in order to individualise a chip comprising the mass spectrometer.

Moreover, the method for manufacturing the system can include the manufacture of at least one microcapillary chromatography column by etching a groove in a substrate, functionalising said groove by a stationary phase, then bonding a cover on said groove.

According to an embodiment, the mass spectrometer and the microcapillary chromatography column are manufactured in separate substrates and the chromatography column and the mass spectrometer are assembled by bonding of the main faces of the substrates wherein they are formed, then said assembled substrates are cut in order to individualise a chip comprising the microcapillary chromatography column and the mass spectrometer.

According to another embodiment, at least one chromatography column is manufactured by etching a groove in the substrate wherein is arranged the flight zone of the ions of the mass spectrometer, functionalising said groove by a stationary phase and bonding of said substrate with another substrate in order to close the ion flight channel and the microcapillary chromatography column.

BRIEF DESCRIPTION OF THE DRAWINGS

Other characteristics and advantages of the invention shall appear in the following detailed description, in reference to the annexed drawings wherein:

FIG. 1 is a block diagram of the system,

FIG. 2 is a block diagram of a preconcentrator,

Figure 3:
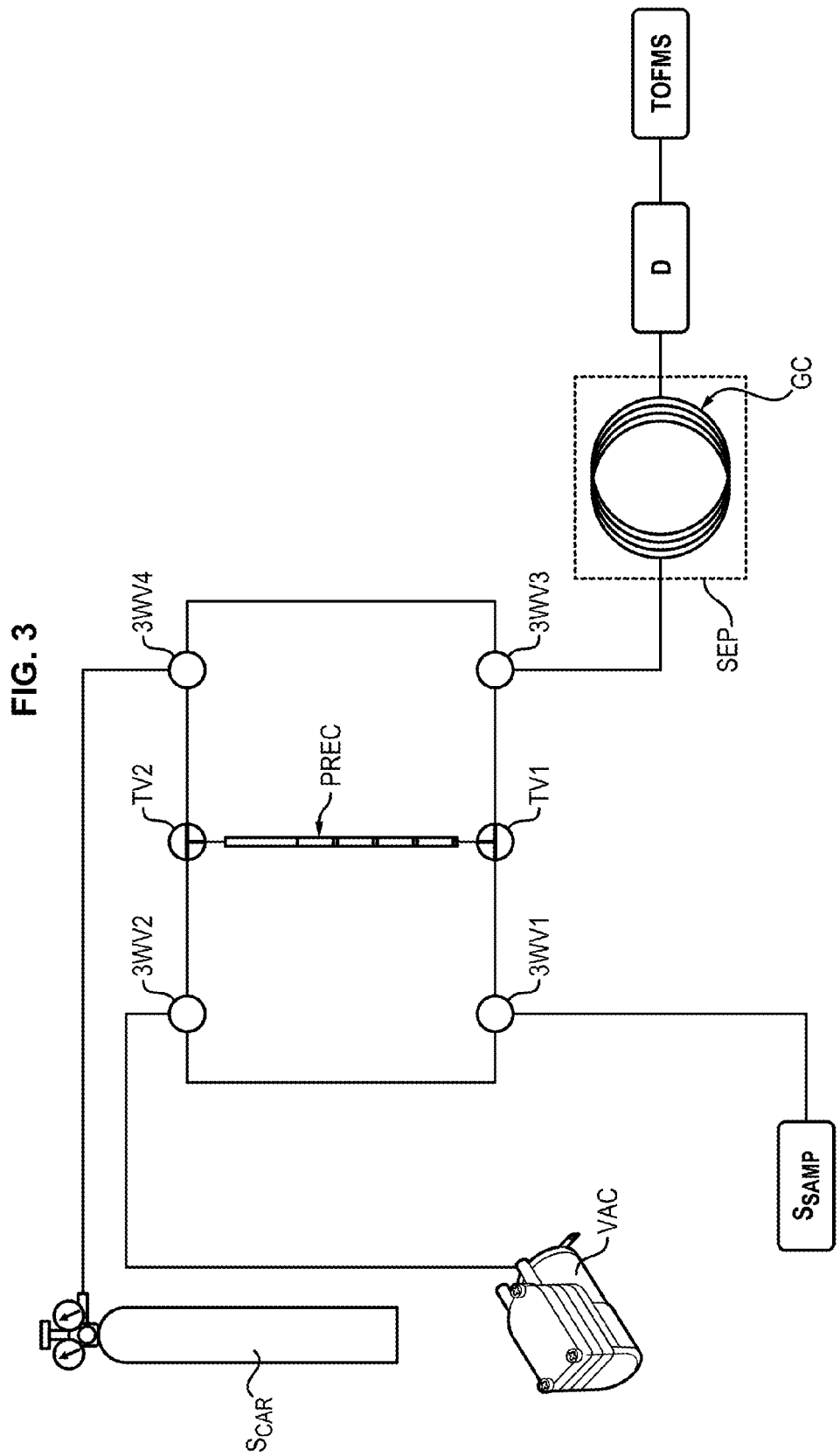
FIG. 3 is a diagram of an embodiment of the circuit for preconcentrating the sample.

For reasons of legibility of the figures, the various elements were not necessarily shown to scale.

DETAILED DESCRIPTION OF THE INVENTION

General Architecture of the System

FIG. 1, in a diagrammatical and non-limited manner, shows the general architecture of the analysis system S.

The sample to be analysed is presented in gaseous form and comprises one or several chemical species to be measured.

For the analysis, a determined quantity of said sample is introduced into an injection device INJ which is coupled to a source $S_{CAR}$ of a carrier gas.

Said carrier gas has for function to transport the species contained in the sample to be analysed in the various components of the analysis system.

The carrier gas is an inert gas with regards to the sample.

The carrier gas is usually chosen from among the following gases, pure or as a mixture thereof: helium, hydrogen, argon, dinitrogen, dry air, filtered (scrubbed) air.

The injection device is also coupled to a source $S_{SAMP}$ of said sample.

According to the context of use of the system, the sample source $S_{SAMP}$ can be a container containing said sample (in particular when the sample was sampled beforehand and transported in order to be analysed) or a duct for conveying a dynamic flow of the sample (constituted for example of a deviation set up on an industrial installation, in particular with a view to a continuous control of an industrial method).

In a manner known per se, the injection device comprises an injection loop which can be closed at its two ends by valves coupled to the sample source and to the carrier gas source.

The injection of gas to be analysed in the system first comprises the introducing of a portion of the sample in the injection loop, then the stopping, by the valves, of the circulation of the sample followed by the introducing in the loop of a determined quantity of the carrier gas, which drives the portion of the sample present in the loop to the analysis system.

Optionally, the injection device INJ further comprises a preconcentrator PREC which shall be described in detail hereinbelow, with a view to concentrate the species in the gas to be analysed.

Such a preconcentrator can be required in particular when it is desired to detect, in the gaseous sample, species that are present only in the form of traces, i.e. with a concentration so low that, in light of the generally low ionization output of the mass spectrometer (which is currently about a few %), they cannot be detected by said spectrometer.

Generally, the use of a preconcentrator is desirable when the concentration of the species to be detected is less than a few tens to a few hundred ppb.

When it is present, the preconcentrator is part of a preconcentration circuit coupled to a module for separating the species contained in the gas to be analysed, said module SEP comprising at least one microcapillary column GC for gas phase chromatography.

In certain embodiments, the separation module can include several microcapillary columns for chromatography connected more preferably in series, although they can also be connected in parallel.

In such a case, the separation module can advantageously further include a modulator in order to manage the flow of the sample through these various columns.

Alternatively, said columns can be provided with at least two non-destructive micro or nano-detectors which provide information on the moments of passing of the various species in each one of said columns.

An example of a module with two columns shall be described in the example no. 2 hereinbelow.

The separation module SEP is coupled with the time-of-flight mass spectrometer TOFMS.

Advantageously but optionally, at least one non-destructive micro or nano-detector D can be placed upstream of the mass spectrometer TOFMS, downstream of the separation module and/or inside said at least one microcapillary chromatography column.

For the design and the coupling of the various components of the system, attention is more preferably given to that the cross section of the fluidic stream wherein the gas to be analysed circulates be regular from the injection device of the sample to the inlet of the mass spectrometer.

Said fluidic stream is of the microcapillary type, i.e. it has a cross section equivalent to the cross section of a circle of 1 mm or less in diameter.

"Regular" means that the cross section of the stream does not have any abrupt variations and that any variations in cross section do not exceed 20 to 30% of the average cross section of the stream.

Indeed, any substantial change in the cross section within the fluidic stream would be able to create dead volumes that are responsible for a dilution of the gas, which could result in a dispersion of the species.

In particular, when a micro or nano-detector is arranged in the fluidic stream travelled through by the gas, a detector is chosen of which the size is adapted in order to not disturb the cross section of the stream.

The nano-detectors, in particular NEMS (Nano Electro-Mechanical Systems) or nano-TCD (Nano Thermal Conductivity Detector) are therefore particularly well suited for this constraint, due to their small size.

This does not exclude a detector of the MEMS (Micro ElectroMechanical System) type, if it is wisely chosen, from also being used without affecting the cross section of the stream.

A particularity of this analysis system, which will be developed in detail hereinbelow, is that the mass spectrometer is arranged in the volume of at least one substrate, in such a way that said spectrometer is particularly compact.

For example, the spectrometer can be carried by assembling two substrates that beforehand were structured in such a way as to form one or several cavities and form various parts of the spectrometer, said spectrometer then extending partially in the volume of each one of said substrates.

This miniaturisation of the mass spectrometer with a good resolution over a wide measuring range is made possible by the integration, between the ion source and the free-flight zone, of a region referred to as micro-reflectron, of which the function is to offset the dispersions of the kinetic energy of the ionized species, which makes it possible to obtain results that can be used despite the short length of the free-flight zone.

Substrate means any material that has for example the form of a wafer or of a chip and able to be structured by micro-manufacturing techniques.

By way of example, silicon substrates, whether they are bulk or constituted of a stack of layers (as for example silicon on insulator (SOI) substrates), are particularly suited for carrying out at least one portion of the mass spectrometer.

Indeed, various micro-manufacturing techniques have been developed for this material and are currently well controlled on an industrial scale, in particular in the field of microelectronics.

These techniques in particular include techniques of photolithography, etching and depositing layers that allow a substrate to be structured by adding or removing material.

However, substrates of materials other than silicon can be used, depending on the function sought.

For example, glass substrates, of SiC, or of a semiconductor material other than silicon, can also be used to carry out certain elements of the system.

Moreover, the separation module comprising one or several columns of microcapillary cross section, it is also very compact, in such a way that the assembled system has a particularly small size.

In a particularly advantageous but not limited manner, the microcapillary chromatography column or columns can also be made in the volume of a substrate, which makes it possible to minimise their size.

It is then possible to manufacture, using micro-manufacturing techniques, the separation module and the mass spectrometer on different substrates, then to associate these components by stacking substrates or through the association of chips obtained by cutting said substrates.

Alternatively, it is possible to manufacture, using micro-manufacturing techniques, a microcapillary chromatography column and the mass spectrometer in the volume of the same substrate.

By cutting substrates, it is as such possible to obtain chips bearing one or several components of the system.

The various components of the gas analysis system shall now be described, whether they are essential or optional.

Preconcentration Circuit

As explained hereinabove, this circuit is optional and is primarily used when the species to be analysed are able to be present with a low concentration in the gaseous sample such that it is injected at the inlet of the system.

In this case, in order to increase the quantity of material to be analysed by mass spectrometry, it is necessary to use a preconcentrator, i.e. a device that makes it possible to provide, using the gaseous sample as it was collected, a more concentrated gaseous sample that will be introduced into the mass spectrometer.

In the analysis system, the preconcentrator PREC is located upstream of the separation module comprising at least one microcapillary chromatography column GC.

It is coupled to said module by a preconcentration circuit which shall be described in detail hereinbelow.

Various types of preconcentrators currently exist on the market and can be used in the scope of this invention.

Generally, the preconcentration is based on a step of trapping species of the sample to be analysed followed by a step of restitution of said species with a view to the analysis, said species then being driven by a carrier gas.

According to an embodiment, the preconcentrator is based on the adsorption/thermo-desorption technique.

As shown in FIG. 2, such a preconcentrator comprises one or several adsorbent beds arranged inside a thin-walled metal tube.

The optimisation of the preconcentration for a single species or a mixture of similar species can be carried out with a single adsorbent bed.

However, in the presence of a complex mixture containing different species, an optimum preconcentration requires the use of several separate adsorbent beds.

Such beds have been described in [5] [6] [7] [8].

The arrangement of the various adsorbent beds in relation to one another is important for the operation of the preconcentrator.

Indeed, if an adsorbent with a high absorption capacity (referred to as "strong adsorbent") is required to trap very volatile species, such an adsorbent is able to retain a less volatile species so strongly that its desorption will be practically impossible.

Inversely, an adsorbent with a lower adsorption capacity (referred to as "weak adsorbent") makes it possible to desorb less volatile species more easily, but will not make it possible to trap the most volatile species.

In practice, the various adsorbent beds are therefore arranged according to an increasing adsorption capacity in the direction of the circulation of the sample in the adsorption phase.

As such, as they pass along the preconcentrator, the most volatile species remain and are adsorbed successively, with the most volatile species being trapped by the last bed, which has the strongest adsorption capacity.

When a gaseous sample to be analysed is passed in this tube, the various species of the sample are adsorbed on one or several adsorbent beds according to the chemical affinity between each species and each bed.

The various adsorbed species are then collected by circulating an inert carrier gas in the tube, in the opposite direction of the prior flow of the sample.

After a duration arranged to allow for the balancing of the flow in the tube following the change in direction, a temperature is applied to the tube containing the adsorbent beds that is suitable for causing the thermal desorption of the trapped species and the driving of said species by the carrier gas to the separation module.

To this effect, an insulated resistive wire coupled to a temperature sensor can be wound around the metal tube containing the adsorbent beds, and heated by the Joule effect.

According to an alternative, a heating sleeve can be placed around the metal tube containing the adsorbent beds.

Alternatively, the metal tube can itself by heated directly by the Joule effect through the circulation of an electric current between its ends, in order to quickly bring the adsorbent beds to the desired desorption temperature.

The interest in implementing the desorption by circulating the carrier gas in the opposite direction of the flow of the sample is to prevent any "memory effect" and improve the desorption.

Indeed, if the desorption were to take place in the same direction as the adsorption, the least volatile species would be driven by the carrier gas onto the strongest adsorbents, where they would be trapped.

In the example of FIG. 2, the preconcentrator PREC is comprised of a metal tube P1 containing four different carbon-based adsorbent beds B1 to B4, separated from one another by a glass wool partition P2.

At the ends of the preconcentrator are arranged two partitions P3 in the form of stainless steel grills that maintain the beds in place in the tube P1.

The arrow SC indicates the direction of the flow of the sample in the step of adsorption (collecting species) and the arrow SD, that of the flow of the carrier gas in the step of desorption (releasing of species).

From upstream to downstream in the direction of the arrow SC, there is for example a first bed B1, of the Carbopack™ Y type, which is that which has the lowest adsorption capacity, a second bed B2 of the Carbopack™ B type, a third bed B3 of the Carbopack™ X type and a fourth bed B4 of the Carboxen 1000 type, which is the one that has the highest adsorption capacity.

In this example, the inner diameter of the tube P1 is 1 mm or less and the mass of each one of the adsorbent beds is about 2 mg.

In the adsorption step, the flow rate of the sample is about 50 to 100 ml/min, at a temperature of 25° C.

In the desorption step, the flow rate of the carrier gas is about 0.8 to 1.5 ml/min at a temperature of 280 to 350° C., for 30 to 180 seconds.

Naturally, any other type of preconcentrator can be chosen without however leaving the scope of this invention.

FIG. 3 diagrammatically shows an embodiment of the preconcentration circuit connecting the sample source $S_{SAMP}$ to be analysed, the carrier gas source $S_{CAR}$ and the preconcentrator PREC itself at the inlet of the separation module SEP.

In the example shown, the separation module comprises a single microcapillary chromatography column GC, but it could also include several columns coupled in series.

This circuit comprises four 3-way valves 3WV1 to 3WV4 and two zero dead volume T-shaped valves TV1 and TV2, which are arranged in such a way as to distribute the flows of the gaseous sample and of the carrier gas in the system according to the adsorption and desorption steps.

Those skilled in the art are able to select the suitable valves from among the valves present in the market.

For example, 3-way valves are marketed by Neptune Research Inc. under the reference HP161031, while zero dead volume T-shaped valves treated by Sulfinert™ are available from Restek under the reference 22534.

The two zero dead volume T-shaped valves TV1 and TV2 are placed at the two ends of the preconcentrator PREC, with the first valve TV1 being located upstream of said preconcentrator in the direction of the flow of the sample in the adsorption phase (and consequently downstream in the direction of the flow of the carrier gas in the desorption phase) while the second valve TV2 is located downstream of said preconcentrator in the direction of the flow of the sample in the adsorption phase (and consequently upstream in the direction of the flow of the carrier gas in the desorption phase).

A first 3-way valve 3WV1 is connected to the source of the sample, to a branch leading to a second 3-way valve 3WV2 and to the first T-shaped valve TV1

The second 3-way valve 3WV2 is in fluidic connection with a vacuum pump VAC and with the second T-shaped valve TV2.

The third 3-way valve 3WV3 is in fluidic connection with the first T-shaped valve TV1, the chromatography column GC and the fourth 3-way valve 3WV4.

This fourth valve 3WV4 is in fluidic connection with the source $S_{CAR}$ of carrier gas and the second T-shaped valve TV2.

Figure 4:
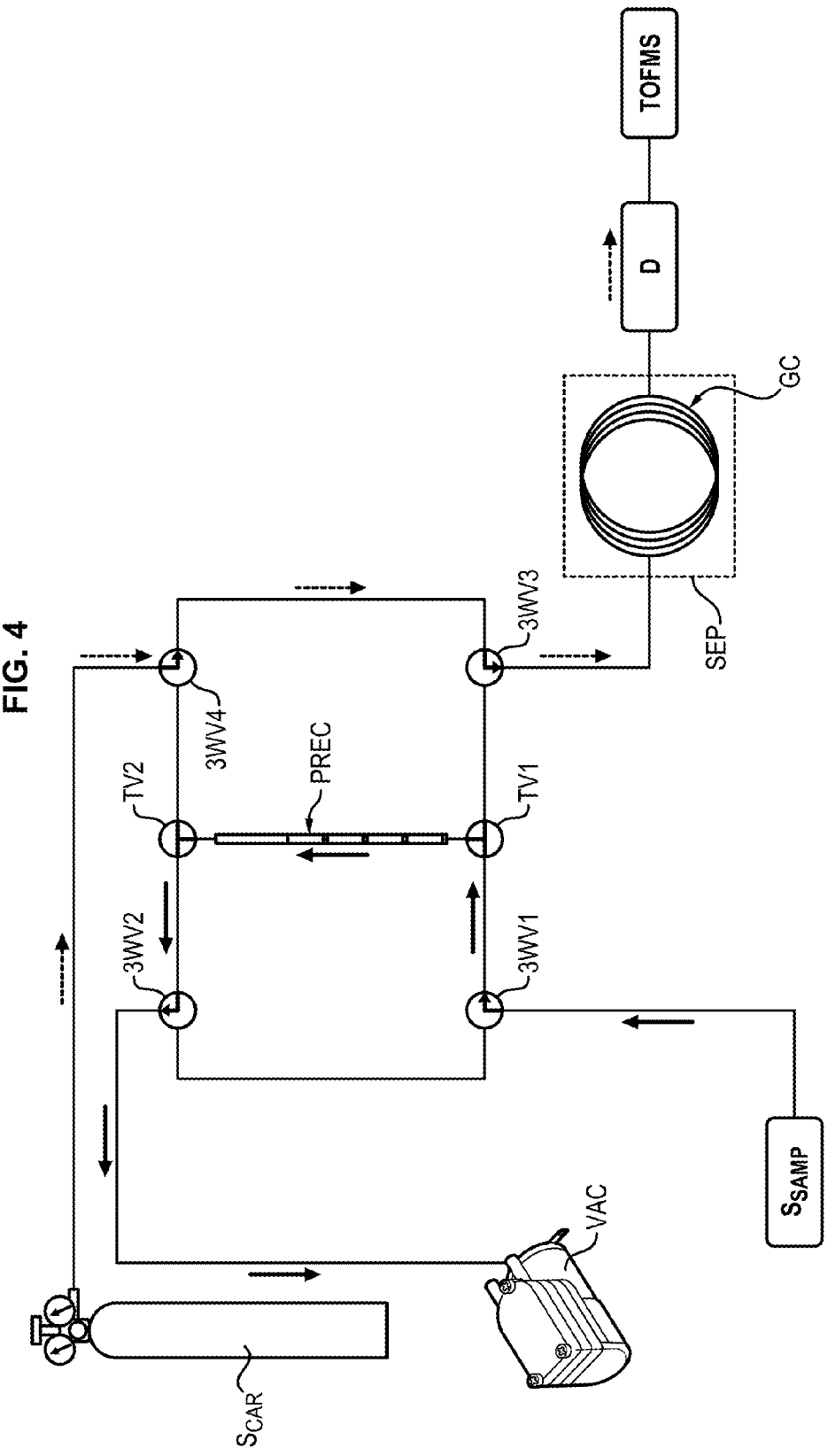
FIG. 4 shows, based on FIG. 3, the flows of gases in the preconcentration circuit in the adsorption phase of the various species present in the sample by the preconcentrator.

FIG. 4 shows the flows of gas in the preconcentration circuit during the adsorption phase.

The arrows with a solid line diagram the flows of the sample; the arrows with a dotted line diagram the flow of the carrier gas.

In this phase, the opening of the 3-way valves 3WV1 to 3WV4 and of the T-shaped valves TV1 and TV2 is controlled in such a way as to allow for the extraction, via the pump VAC, of the sample starting from its source $S_{SAMP}$ and its passage through the preconcentrator PREC (in the direction of the first T-shaped valve TV1 to the second T-shaped valve TV2, i.e. the direction of the arrow SC in FIG. 2) in order to allow for the adsorption of its species.

Those skilled in the art are able to determine the volume of the sample to pass through the preconcentrator according to the particular system used.

This volume is typically controlled through the duration of the adsorption phase.

The temperature of the adsorbent beds also has an impact on the effectiveness of the preconcentration.

Advantageously, the preconcentrator is designed in such a way as to allow for an effective adsorption at ambient temperature (25° C.).

Simultaneously, the opening of the 3-way valves is controlled in such a way as to allow for the circulation of the carrier gas from its source $S_{CAR}$ to the inlet of the chromatography column, in an isolated way from the flow of the sample.

In this phase, the inert carrier gas also passes through the microcapillary chromatography column GC, where applicable, the micro or nano-detector D and the mass spectrometer TOFMS, without measurements being taken.

Figure 5:
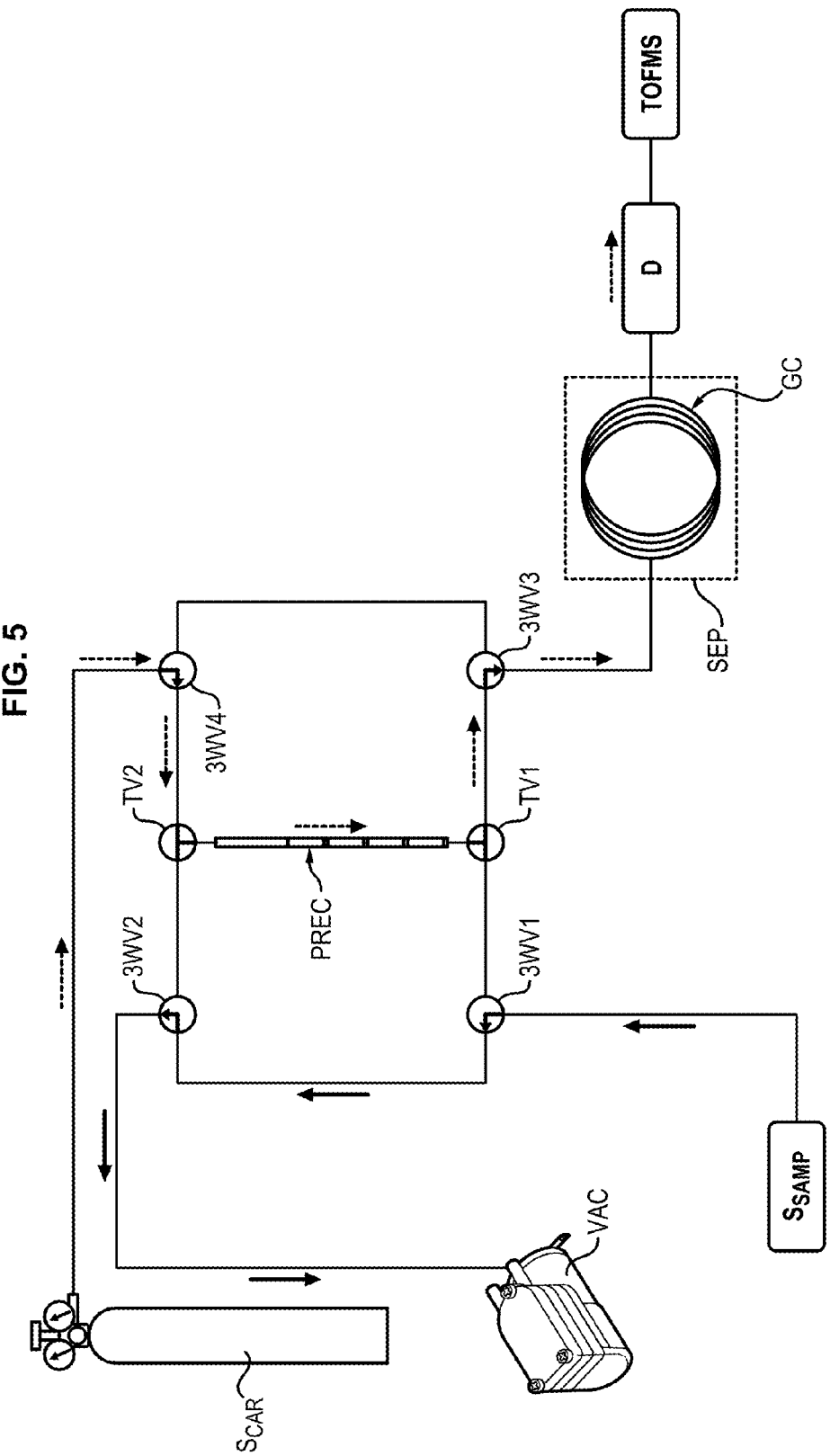
FIG. 5 shows, based on FIG. 3, the flows of gases in the preconcentration circuit in the desorption phase of the various species adsorbed beforehand by the preconcentrator.

FIG. 5 shows the flows of gas in the preconcentration circuit during the phase of thermo-desorption.

In this phase, the opening of the 3-way valves and of the T-shaped valves is controlled in such a way as to deviate the sample from the preconcentrator PREC and to allow for the passing of the carrier gas in said concentrator.

When the sample comes from a dynamic source $S_{SAMP}$, the sample is sucked by the pump VAC, which then operates continuously during the two steps of preconcentration.

When the source $S_{SAMP}$ of the sample is a container, the pump VAC is more preferably stopped during the step of desorption, in order to retain in the container the unsampled portion of the sample. In this case, no extraction of the sample takes place during the thermo-desorption phase.

Simultaneously, the opening of the 3-way valves and of the T-shaped valves is controlled in such a way as to allow for the circulation of the carrier gas from its source $S_{CAR}$ through the preconcentrator PREC (in the direction of the second T-shaped valve TV2 top the first T-shaped valve TV1, i.e. in the direction of the arrow SD in FIG. 2), with a view to the desorption of the species of the sample trapped during the adsorption phase, as the flow of the carrier gas is still isolated from the flow of the sample.

In this phase, the carrier gas containing the species of the sample, with higher concentrations than in the initial sample, then passes through the chromatography column GC, where applicable, the micro or nano-detector D and the mass spectrometer TOFMS, in order to allow for the taking of the measurements.

Separation Module

The separation module comprises at least one microcapillary gas phase chromatography column.

Said microcapillary chromatography column can be formed, conventionally, by a tube made from a chemically inert material, for example a silica tube.

Said column has a cross section equivalent to the cross section of a circle that has for example a diameter between 10 µm to a few hundred micrometres, even up to 1 mm or slightly more.

The length of the column is for example between 0.2 m and a few metres.

In order to provide the column with a limited size, the microcapillary tube can be wound on a mandrel, with the diameter of said mandrel having to be sufficient in order to avoid any breakage of the tube.

Alternatively, the microcapillary column can be carried out in the volume of a substrate, for example a silicon substrate.

A method for manufacturing such a column is described hereinbelow.

Regardless of the embodiment, the inner surface of the microcapillary column is covered with a thin film of a material called the stationary phase.

The depositing of such a material can be carried out by any type of technique known to those skilled in the art, such as liquid phase deposition or a gaseous phase deposition (in particular by chemical vapour deposition (CVD), physical vapour deposition (PVD) or spraying ("sputtering")).

The material for the stationary phase can be for example a polymer, such as polyethylene glycol or polydimethylsiloxane.

This material can also be a porous solid, a sol gel, or a liquid.

The various species of the sample injected will separate according to their affinities with the stationary phase, as certain species are slowed down more than others, which will make it possible to measure the signal emitted by the various molecules with a view to identifying them.

For a given column, a species is defined by a coefficient or retention factor usually noted as k.

This retention factor corresponds to the ratio between the mass of the species in the mobile phase over the mass of the species in the stationary phase. It is also the ratio between:
- the difference in the respective transit durations of the species and of the solvent,
- and the duration of the transit of the solvent (here, the carrier gas), which does not have any interaction with the column, in the column.

A species that has a strong retention factor corresponds to a species that is substantially slowed down, having a strong affinity with the stationary phase of the column.

Figure 6:
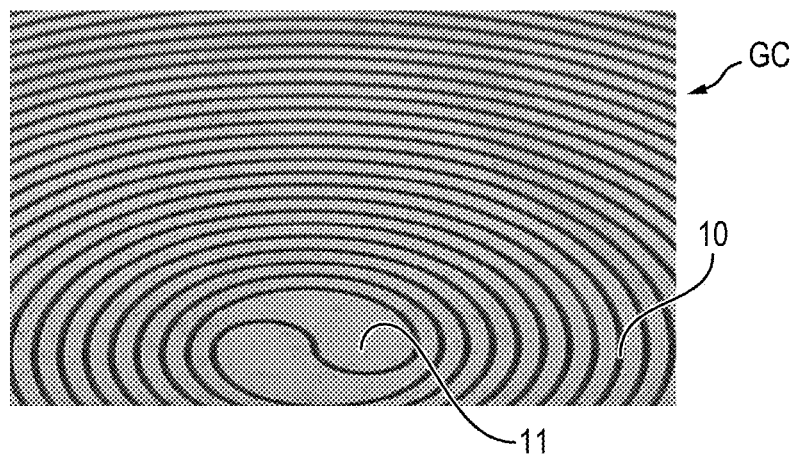
FIGS. 6 and 7 are respectively top and cross-section views of a microcapillary chromatography column arranged in the volume of a silicon substrate.
Figure 7:
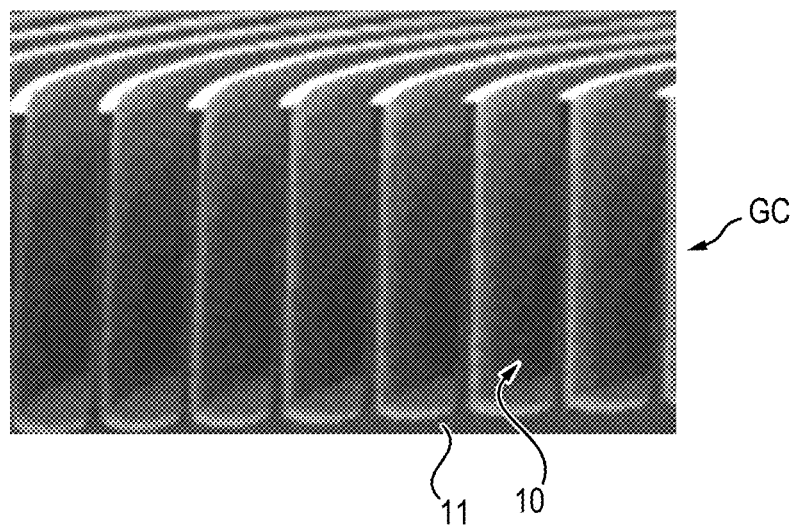

FIGS. 6 and 7 show top and longitudinal cross-section views of an example embodiment of a microcapillary chromatography column GC in the form of two spirals wound one within the other.

This column is carried out by etching a groove 10 in a planar substrate 11, for example of silicon, via conventional microelectronic techniques that combine the steps of photolithography and deep etching.

Over a surface of a few square centimetres, it is thus possible to carry out a column:
- of which the cross section is determined by the depth of the etching and the width of the etching. Each one of these dimensions can vary from around ten to a few hundred microns,
- of which the length can range from a few tens of centimetres to one or several metres, for example two metres.

The spiral shape makes it possible to ensure that the minimum radius of curvature is large enough to minimise the dispersion of the elution bands in the conditions of flow implemented during the separation.

However, the groove can follow a path other than that of a spiral.

Once covered with the stationary phase, the groove etched in the substrate 11 is closed with a cover (not shown here).

Said cover is for example made of silicon, silica or glass (for example Pyrex®), where applicable covered with the stationary phase.

The fastening of the cover onto the substrate is obtained using a method known in conventional microelectronics, for example via molecular bonding or anodic bonding.

It can also be considered to glue the cover on the substrate by means of a glue deposited via silkscreen or by means of a dry film (resin, for example Ordyl™)

Particularly advantageously, a plurality of microcapillary columns are formed on a substrate collectively.

This means that, on a substrate that typically has the form of a wafer 200 mm in diameter, a plurality of separate grooves regularly distributed over the surface of the wafer are created simultaneously, then the selected stationary phase is deposited simultaneously on the walls of all of said grooves.

The depth of the grooves is generally controlled by the duration of the etching.

A particular form of execution can consist in using an SOI (Silicon On Insulator) wafer, i.e. comprised of a silicon active layer, a buried silicon oxide layer a few µm thick and a silicon support layer that has the desired thickness for the depth of the column (typically, a few hundred µm).

The grooves can thus be etched into the silicon support layer, with the buried oxide layer forming an etching stop layer, which makes it possible to control the depth of all of the grooves.

An example of a PDMS or PEG stationary phase deposition is described in [10].

Then, the grooves are closed by fastening onto the wafer forming the substrate a wafer forming a cover and typically having the same diameter as the substrate.

Alternatively, it is possible to proceed with an individual adding of covers on each groove etched as such.

After this assembly, chips each containing one chromatography column are individualised by cutting.

According to an example implementation, the groove 10 has a rectangular cross section 30 µm wide by 685 µm deep, but it goes without saying that these values are provided solely for the purposes of information.

Mass Spectrometer

Figure 8:
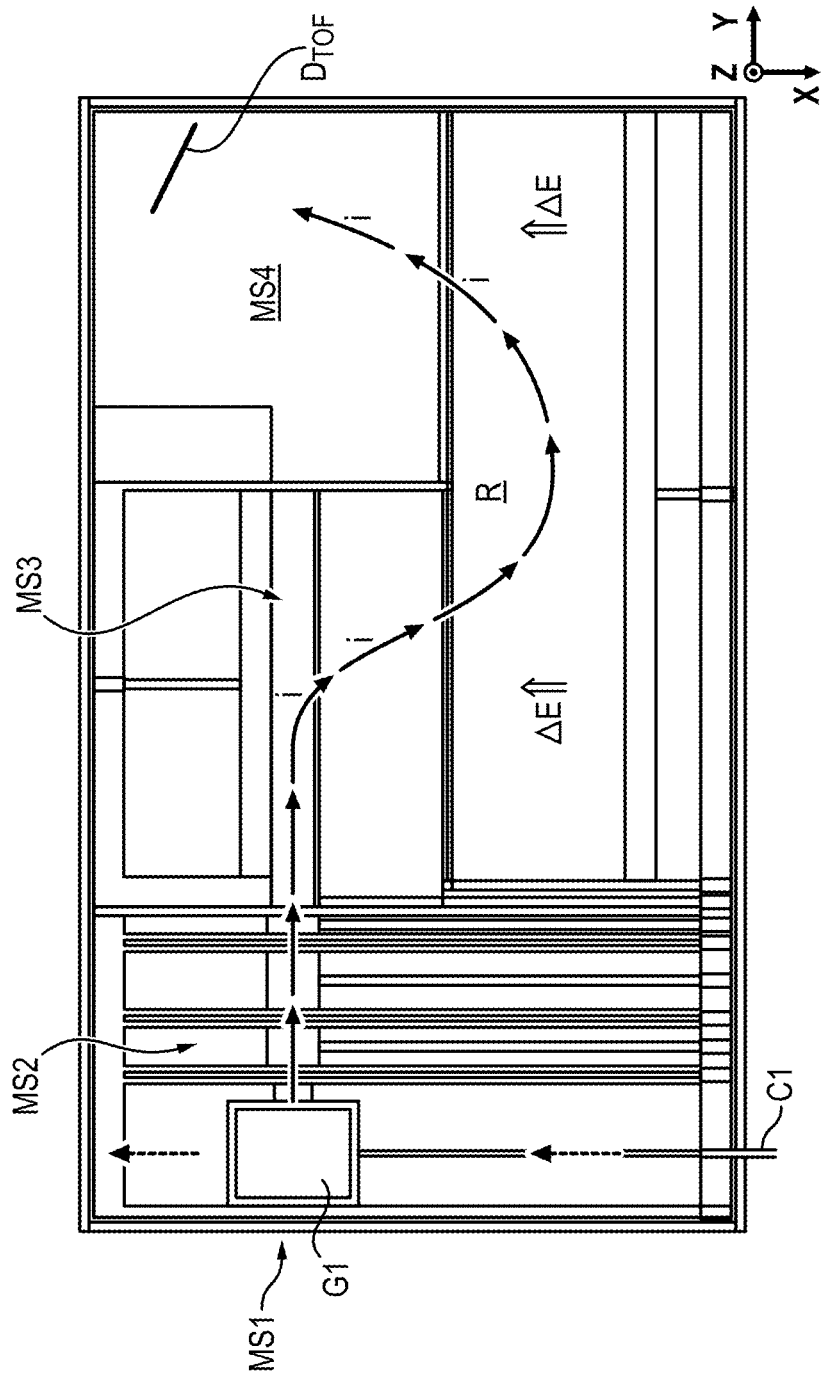
FIG. 8 is a top view showing the general architecture of the time-of-flight mass spectrometer.

FIG. 8 shows, as a top view, the architecture of the time-of-flight mass spectrometer TOFMS, wherein the trajectory of the ions is diagrammatically shown by the arrows i.

Said spectrometer comprises several zones which, from upstream to downstream, are the following:
- a chamber MS1 for ionizing species separated beforehand by the chromatography column, with the inlet of the gas into said chamber coming from the separation module being carried out by a microcapillary tube C1,
- a zone MS2 for ionic focussing, with the chamber MS1 and the focussing zone MS2 together forming an entity referred to as the ion source,
- a zone MS3 for accelerating ions,
- a micro-reflectron, R wherein there is an electrostatic field gradient $\Delta E$ transversal to the trajectory of the ions, making it possible to modify the trajectory of the ions upstream of the free-flight zone,
- a free-flight zone MS4 (or "drift zone"), which is a zone devoid of any electrostatic field,
- at the end of the free-flight zone MS4, one or several ion detectors $D_{TOF}$.

The various zones of said mass spectrometer have the particularity of being arranged in the volume of a substrate, thanks to micro-manufacturing techniques used in particular in the field of microelectronics.

Ion Source

The carrier gas driving the species to be analysed is introduced into the mass spectrometer via a microcapillary tube C1 that connects the separation module and the inlet of the ionization chamber MS1, with the flow of the gas being oriented according to the axis x.

According to an embodiment, the ionization is carried out via electronic bombardment of the gaseous species, with the carrier gas not being substantially ionized.

The electrons are for example emitted by a heated tungsten filament (emission via thermo-ionization) and accelerated with an energy of 70 eV via an electrostatic field applied between the grill G1 arranged in the ionization chamber MS1 in order to attract the electrons and the heated filament.

This energy of 70 eV makes it possible to achieve the optimum ionization output for gaseous species.

In order to prevent damaging the tungsten filament due to the high temperature, the silicon chip wherein is manufactured the mass spectrometer, it can be necessary to interpose a heat screen between the filament and the wall of the chip.

Alternatively, instead of the tungsten filament, the emission of the electrons can be carried out by a cold source of the Micro Channel Plate (MCP) type.

These plates are known per se and therefore will not be described in detail here.

These plates can advantageously be cut to the desired dimension, i.e. more preferably that of the ionization chamber, and are not voluminous.

Preferably, the ions exit the ionization chamber MS1 in a direction (here, according to the axis y) orthogonal to the inlet direction of the gas, which makes it possible to increase the sensitivity and the resolution of the system, as compared to a direct injection, i.e. according to the inlet direction of the gas in the spectrometer.

As the carrier gas has a negligible ionization output, it is practically not deviated and is removed in the axis of the inlet of the mass spectrometer, i.e. according to the axis x (the flow of gas is diagrammed, in this figure, by an arrow with a dotted line).

By injecting the ions in a direction perpendicular to the direction of the flow of the carrier gas, the latter is prevented from disturbing the trajectory of the ions in the downstream portion of the spectrometer; a more stable measuring system is therefore obtained.

Such an orthogonal injection is obtained by applying potentials that are adapted to the electrodes of the ionization chamber and of the focussing chamber.

Figure 9:
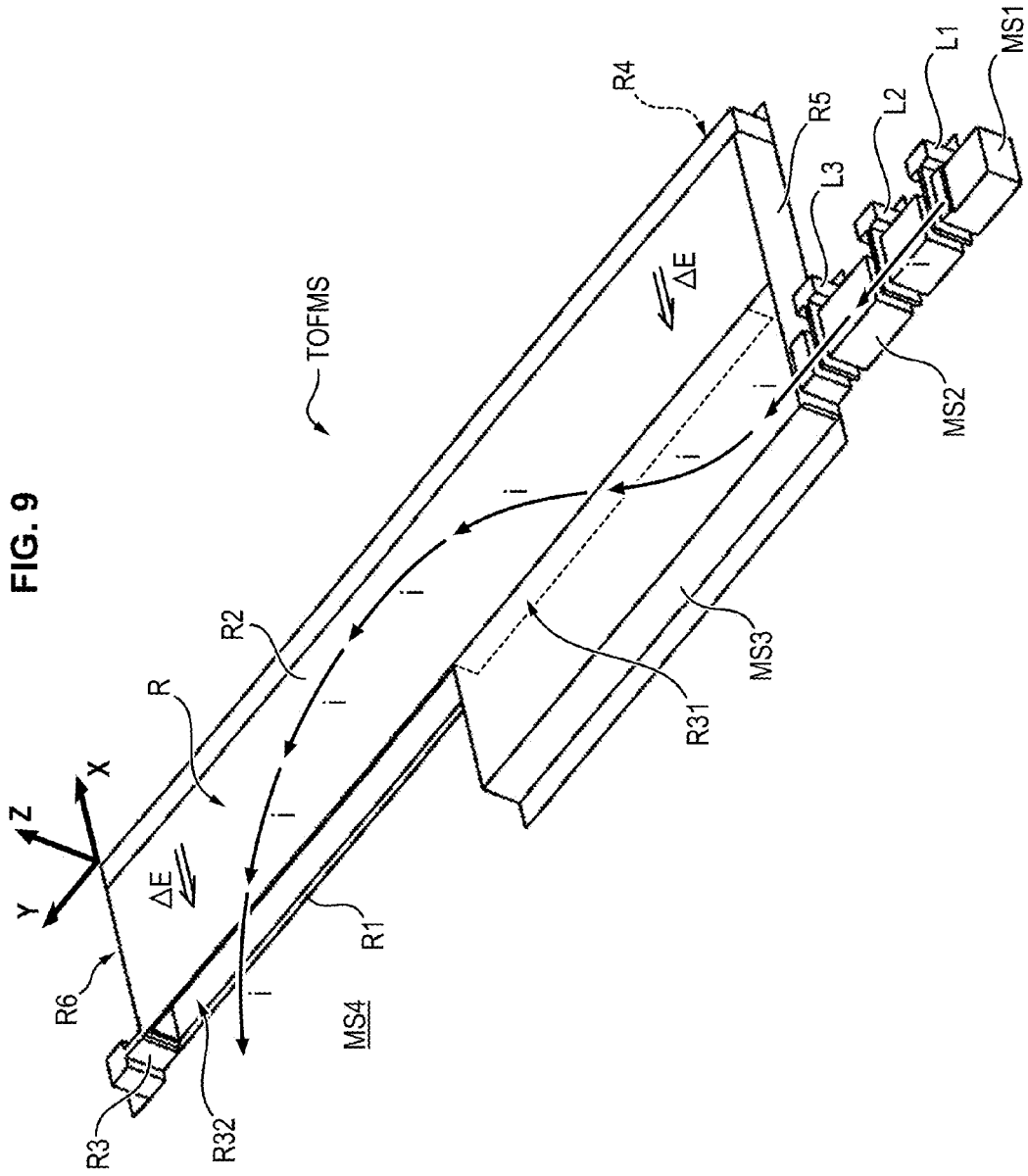
FIG. 9 is a perspective view of the various elements of said spectrometer.

The ions pass from the ionization chamber MS1 to the focussing chamber MS2 which comprises a known device constituted of electrostatic lenses referred to as Einzel, indicated by marks L1 to L3 in FIG. 9, making it possible to focus all of the ions according to a beam with a given cross section with collinear velocity vectors.

For example, the task of diffraction of said focussed beam is about 100 μm or less at the inlet of the acceleration zone MS3.

Acceleration Zone

The acceleration of the ions is obtained between two electrodes (designated by the marks E31 and E32 in FIG. 10), extending parallel to the direction y of the ion beam produced by the source MS1, MS2.

A voltage of a few tens of volts, for example 20V, is applied between said electrodes, which are typically separated by an interval of a few mm, in order to procure a nominal speed that is greater than that of the Brownian motion.

This corresponds to an energy of a few mJ to a few tens of mJ for example.

The polarisation of the electrodes has for effect to deviate the ions coming from the source by pushing them back according to a substantially orthogonal direction (i.e. here, according to the axis x), in order to direct them to the micro-reflectron R.

Particularly advantageously, said electrodes are polarised in a pulsed manner, in such a way as to sequentially inject the ionised species in the downstream portion of the spectrometer intended for detection.

In other terms, the ions enter the downstream portion of the spectrometer only during the durations of polarisation of said electrodes E31, E32.

Thanks to this pulsed polarisation of the electrodes, a time sampling of the elution peak coming from the separation module by carrying out spectrometric analyses on a series of very small intervals in light of the duration of the peak (10 times to 1000 times shorter for example). The elution peak is reconstructed in this way, interval by interval.

Alternatively, other means can be used, for example electromechanical devices placed upstream of the source (such as quick solenoid valves which are usually used in mass spectrometers), in order to carry out such a time segmentation.

However, the use of pulse-controlled electrodes makes it possible to obtain sampling frequencies that are much higher than those of electromechanical devices.

Micro-reflectron

The mass spectrometer comprises a micro-reflectron that makes it possible, thanks to an electrostatic field gradient oriented transversely to the trajectory of the ions, to increase the duration of the travel of the ions and to offset the kinetic dispersion of the ions due to the imperfections of the ion source, which is indispensable in order to preserve a good resolution in a small-size mass spectrometer wherein the time and space dispersions cannot be neglected.

Thanks to such a micro-reflectron, the resolution power passes from 50 to 2000.

Indeed, if ions of a given mass are taken into account, the most energetic ions have a longer trajectory than less energetic ions, in such a way that in the absence of the micro-reflectron, ions of the same mass would reach the detector $D_{TOF}$ at different times.

The micro-reflectron however has a time focal plane, wherein all of the ions of the same mass arrive at the same time, regardless of their initial energy.

FIG. 9 is a perspective view of the volumes of the various elements of the mass spectrometer TOFMS, not showing the substrate whereon they are formed or the various electrodes that make it possible to apply the potentials required for the operation of the various zones of the mass spectrometer.

The inner volume of these various elements forms a circulation channel (or flight) for the ions.

The main face of said substrate is parallel to the plane (x, y), with the direction z defining the thickness of the various elements.

In all of the figures, the mark (x, y, z) is oriented in the same was as in FIG. 8.

The micro-reflectron R has a generally tubular shape with a rectangular cross section of which the faces are designated by the marks R1 to R6.

As shall be seen hereinbelow, some of these faces can be continuous material surfaces, forming walls, or perforated walls comprising one or more openings, for example in order to allow for the passing of ions.

The longitudinal direction of the micro-reflectron is defined by the largest dimension of said micro-reflectron.

The micro-reflectron R comprises two main opposite faces R1, R2 parallel to the main face of the substrate, i.e. to the plane (x, y) and extending longitudinally in the direction y.

The micro-reflectron R further comprises two longitudinal faces R3 and R4 parallel to the plane (y, z) and perpendicular to the main faces R1 and R2.

The two ends of the tube forming the micro-reflectron are defined by two transverse faces R5, R6 parallel to the plane (x, z).

For the purposes of information, the length of the micro-reflectron, which is defined by the dimension of the faces R1, R2 according to the axis y, can be about 1 to 3 cm; the width of the reflectron, which corresponds to the dimension of the faces R5, 56 according to the axis x, can be about 1 mm, and the thickness of the reflectron, which corresponds to the dimension of the faces R3, R4 according to the axis z, is between 400 µm and 1 mm.

The longitudinal face R3 comprises a first opening R31 for the inlet of the ions coming from the acceleration zone MS3, and a second opening R32 for the outlet of the ions to the free-flight zone MS4.

In other terms, the free-flight zone MS4 is adjacent to the acceleration zone MS3, said zones being arranged along the longitudinal wall R3 of the micro-reflectron R.

The trajectory of an ion in the mass spectrometer is shown by the arrows i.

In the ionization chamber MS1 and the focussing zone MS2, the ions circulating in the direction y, which, as explained hereinabove, is the direction orthogonal to which the gas was introduced into the mass spectrometer (the microcapillary tube C1 was not shown in this figure but it is arranged upstream of the ionization chamber MS1 according to the axis x.)

In the acceleration zone MS3, the ions are more preferably deviated in order to be injected in the micro-reflectron in a direction substantially orthogonal to their direction in the source MS1, MS2, i.e. in the direction x.

The ions accelerated in the zone MS3 enter the micro-reflectron R by the first opening R31 of the longitudinal face R3.

In practice, when they enter the micro-reflectron, the trajectory of the ions has an angle in relation to the axis x, in such a way that their velocity vector comprises both a component according to the axis x and a component according to the axis y.

The trajectory of the ions in the micro-reflectron is carried out in the longitudinal direction, i.e. parallel to the axis y and to the direction according to which the ions exit the source MS1, MS2.

Under the effect of the electrostatic field gradient present in the micro-reflectron (which is diagrammed via the double arrow $\Delta E$) in the transverse direction to the trajectory of the ions in the reflectron, the component of the velocity vector according to the axis x in reversed progressively, in such a way that the ions travel through the reflectron in the longitudinal direction therein still being directed first to the face R4 opposite the face R3 through which they entered, then by moving away from said face R4 under the effect of the repulsive force generated by the field gradient $\Delta E$.

In this respect, it is not important that the face R4 be a solid or hollowed out, in that it is the electrostatic field gradient $\Delta E$ that prevents the ions from leaving the reflectron in the direction x.

During their travel in the reflectron, the ions then arrive on the second opening R32 of the face R3, through which they enter into the free-flight zone MS4.

In such a micro-reflectron, the electrostatic field gradient is generated by the polarisation of the resistive layer formed on the face R1, which is designed to be polarised between at least two regions, for example by means of electrodes placed in contact with said regions.

"Resistive" means a material of which the electrical resistivity is at least 1 kOhm·cm.

For example, the resistive layer can be formed from amorphous silicon, even from polycrystalline silicon, and is furthermore slightly doped (i.e. with a concentration in doping less than $10^{19}$ cm$^{-3}$), in order to improve the electrical contact with metal electrodes which make it possible to polarise it.

Moreover, said layer is locally strongly doped (i.e. with a concentration in doping greater than $10^{19}$ cm$^{-3}$) in order to obtain an ohmic contact with the metal electrodes which makes it possible to polarise it.

Said resistive layer extends parallel to the trajectory of the ions in the micro-reflectron.

Particularly advantageously, the resistive layer on the face R1 forms a planar wall, i.e. without protuberances towards the inside of the micro-reflectron, and smooth, i.e. typically having a roughness of less than 1 µm RMS.

As such, said wall does not generate any disturbance in the trajectory of the ions despite the very small cross section of the flight channel.

In particular, the electrodes that make it possible to polarise the resistive layer are advantageously arranged outside of the micro-reflectron.

In order to facilitate the understanding of FIG. 9, the electrodes of the micro-reflectron R and of the zones MS1 to MS3 upstream of the latter were not shown.

Figure 10:
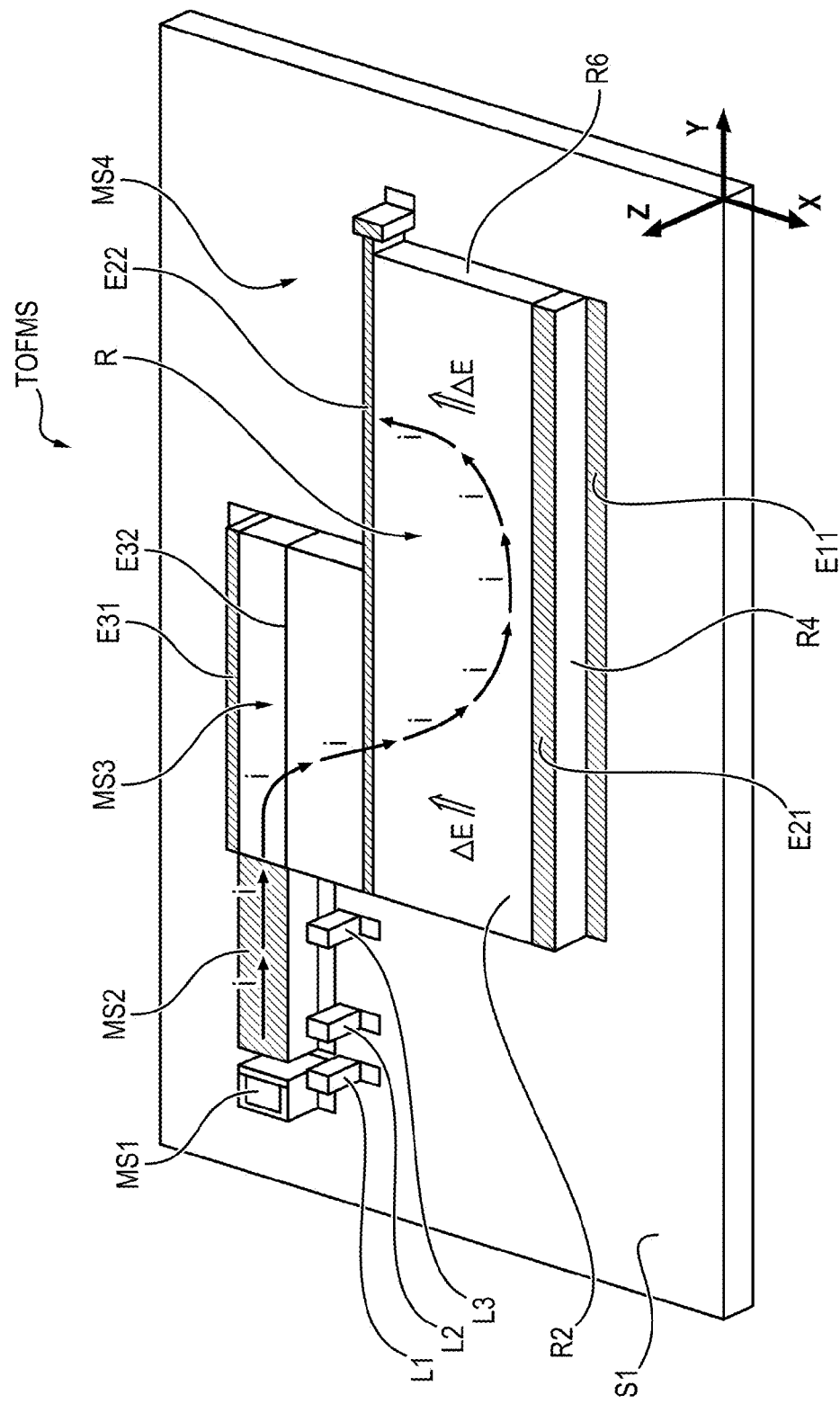
FIG. 10 is a perspective view of said spectrometer presented on a substrate support.

The electrodes are however shown diagrammatically by hashes in FIG. 10, which is a perspective view of the elements of the mass spectrometer TOFMS.

The elements of the mass spectrometer are here shown on a substrate S1, which is for example a glass substrate.

In FIG. 10, the main face R1, opposite the main face R2, is not visible.

It is on this face R1 that the resistive layer mentioned hereinabove is formed.

This layer can be polarised by means of two longitudinal electrodes, extending according to the axis y and placed along the two longitudinal sides of said layer.

In the embodiment shown here, the first longitudinal side of the resistive layer corresponds to the intersection with the longitudinal face R3 and the second longitudinal side corresponds to the intersection with the longitudinal face R4.

The distance between said electrodes is therefore at most equal to the width of the resistive layer, in such a way as to polarise the resistive layer over its entire width; however, it would be possible to bring said electrodes close together, in such a way as to polarise only the portion of the resistive layer between said electrodes, or insert one or several additional parallel electrodes, which would make it possible to choose the portion of the resistive layer to be polarised.

In FIG. 10, only the electrode E11, placed along the second longitudinal side of the resistive layer, can be seen. However, another electrode extends, parallel to the electrode E11, along the first longitudinal side of said resistive layer.

Said polarising electrodes of the resistive layer are advantageously arranged between the substrate S1 and the resistive layer of the face R1, i.e. outside of the micro-reflectron R, in such a way that they do not exit into the inner volume of the micro-reflectron.

When a voltage is applied between said electrodes, a continuous potential gradient is created in the resistive layer, which generates an electrostatic field gradient in the volume of the micro-reflectron as well as in the resistive layer itself due to Ohm's law, in the direction opposite the trajectory x of the ions at their inlet into the micro-reflectron.

Under the effect of this electrostatic field gradient, the ions circulating in the micro-reflectron R are slowed down then change trajectory by moving away from the wall R4.

The face R2 opposite the resistive layer of the face R1 also forms a continuous wall, whereon are arranged two electrodes E21, E22 extending in parallel to the other polarising electrodes of the resistive layer of the face R1, along the two longitudinal sides of the wall R2.

These electrodes make it possible, in comparison with the polarising electrodes of the resistive layer of the face R1, to confine the electric field in the micro-reflectron.

According to a preferred embodiment, the faces other than the face R1 are generally walls made from a material that has an electrical resistivity lower than that of the resistive layer; said less resistive material is chosen in such a way that the walls formed from this material have a global electrical resistance of the same magnitude as the resistance of the resistive layer, in light of the difference in thickness between the resistive layer which is substantially thinner (for the purposes of information, about from 100 to 500 nm, for example 200 nm) than the walls of the faces R2 to R6 of the reflectron (of which the thickness is about 100 μm).

For example, the walls of the micro-reflectron other than the resistive layer of the face R1 can be formed from silicon that has a resistivity of about a few Ohm·cm.

The distance between the polarising electrodes of the resistive layer and the polarisation voltage are dimensioned in order to obtain correct compensation for the dispersion for the ions having the largest mass.

This dimensioning can be done using a simulation software, for example the ANSYS software, which simulates the trajectory of the ions according to finite elements method. Other software such as SIMION, which is dedicated to calculating trajectories of mass loading particles, can be used.

Figure 11:
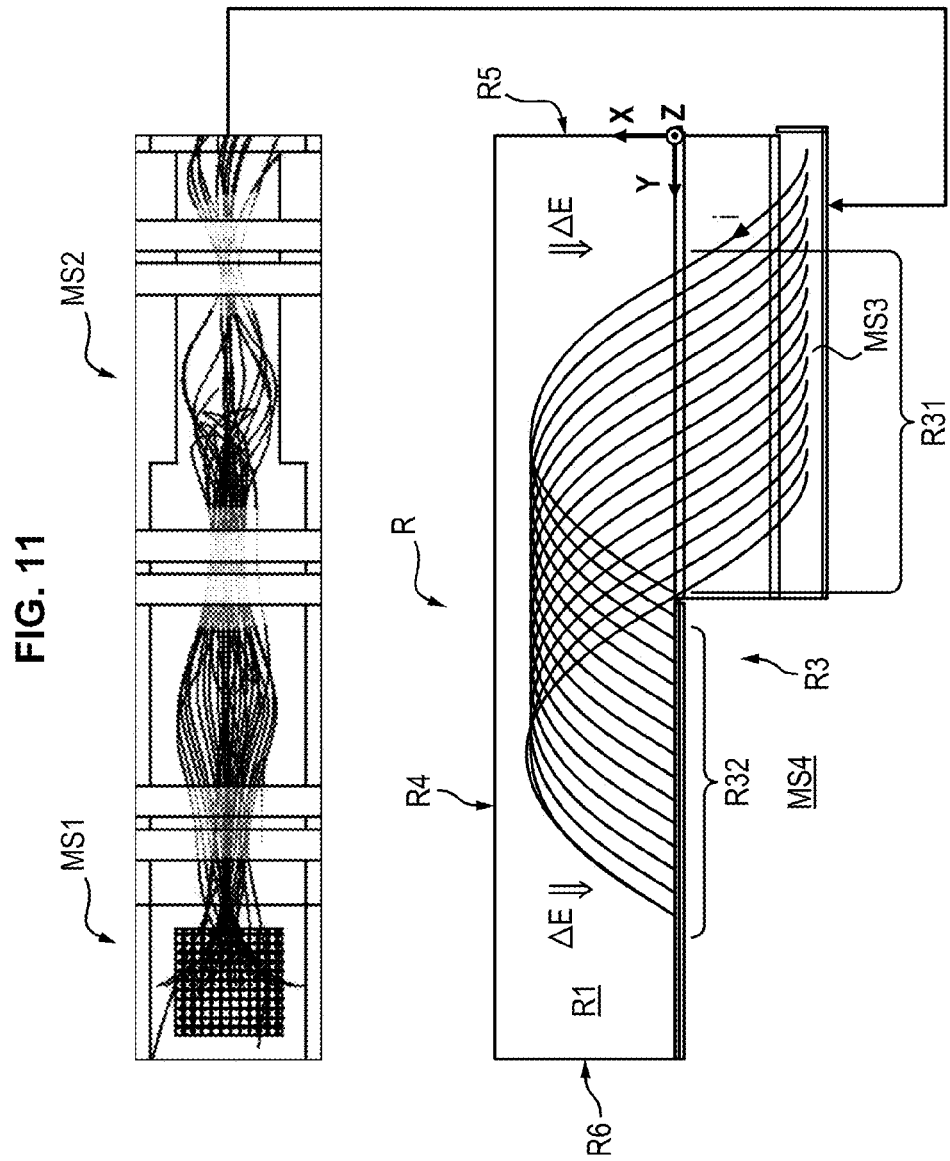
FIG. 11 shows the trajectory of the ions in the spectrometer simulated by finite elements.

FIG. 11 comes from such a simulation and shows the trajectory of the ions in the various elements of the mass spectrometer.

Possibly, the micro-reflectron could include more than two electrodes for polarising the resistive layers of the face R1, although this does not appear to be necessary due to the small size of the device.

The micro-reflectron allows ions that have the same mass to charge ratio, but different kinetic energies, to arrive at the detector $D_{TOF}$ at the same time.

There is indeed a position, downstream of the reflectron, where the penalty in time imposed on the most energetic ions exactly offsets the advantage that the latter initially had on the less energetic ions.

It is this position, referred to as the time focussing plane of the ions of the same m/z ratio, which is generally found in the free-flight zone MS4, where the detector $D_{TOF}$ is placed.

Generally, said time focal plane is located a few mm, even a few cm, from the outlet of the micro-reflectron.

For the purposes of information, the high-resolution mass spectrometers present on the market have a reflectron of which the length is about 20 to 30 cm, which imposes a substantial size. In addition, the distance between the outlet and the focal plane of these reflectrons is about several tens of centimetres.

Moreover, these reflectrons are constituted of an assembly of discrete annular electrodes connected by electrical resistances, which consume a lot of energy.

Miniaturising the reflectron makes it possible to substantially increase the resolution power, i.e. up to values from 1000 to 2000, in relation to existing miniaturised mass spectrometers.

Furthermore, due to the small dimensions of the resistive layer, the energy consumption of the micro-reflectron is much less than that of existing reflectrons.

This decrease in the size therefore authorises the use of a continuous resistive layer.

Moreover, manufacturing in the volume of the same substrate all of the elements of the mass spectrometer, from the ion source to the free-flight zone, makes it possible to control the positioning and aligning of them, without requiring any device for connecting the various elements.

Thus, the structure of the mass spectrometer can be qualified as monolithic, in that it is based only on techniques of micro-structuring substrates and requires no mechanical assembly of components.

In FIGS. 8 to 10, the mass spectrometer comprises a single micro-reflectron.

However, it is not excluded to place in series at least two micro-reflectrons, in order to further increase the resolution power of the mass spectrometer.

In order to avoid time dispersions, the second micro-reflectron must be placed in the time focal plane of the first.

In this case, it is more preferably arranged that the time focal plane of the first reflectron coincides with its planar outlet.

The focal of all of the micro-reflectrons corresponds to the free-flight zone of the mass spectrometer and defines the location of the detector $D_{TOF}$.

Free-flight Zone

The free-flight zone MS4, which is separate from the micro-reflectron and which is arranged at the outlet of the latter, is a zone without any electrostatic field and is therefore typically devoid of electrodes.

Said free-flight zone MS4, of which the length is at least a few cm, allows for the free propagation of the ions, which each possess its own weight and consequently a different kinetic energy.

The ions therefore arrive separated in terms of time according to their mass, on the detector $D_{TOF}$ placed at the outlet of the free-flight zone.

Said detector is generally not placed parallel to the outlet orifice of the micro-reflectron, but with an angular orientation in relation to the latter, as is shown diagrammatically in FIG. 8.

Advantageously, the detector is a counter of ions of the "Faraday Cup" type.

Such a detector can indeed be integrated into a silicon chip.

As such, it can be manufactured at the same time as the flight channel for the ions, in the volume of the same substrate.

In this case, the detector is formed from an element made of silicon that is strongly doped (i.e. with a concentration greater than $10^{19}$ cm$^{-3}$) and polarised, of which the current flowing is measured due to the supply of ions.

Naturally, other types of detectors can be used without however leaving the scope of the invention, for example of the Channeltron or micro channel plate type.

All of the zones described hereinabove are manufactured in or on a chip, for example made of silicon, of which the surface is of a few cm$^2$.

Said chip is then connected on a printed circuit board 103 (cf. FIG. 12) in order to electrically connect the various electrodes to a control electronics.

Said board, as well as the source of electrons 104 and the detector DTOF is then placed in a sealed case wherein a vacuum can be created.

Figure 12:
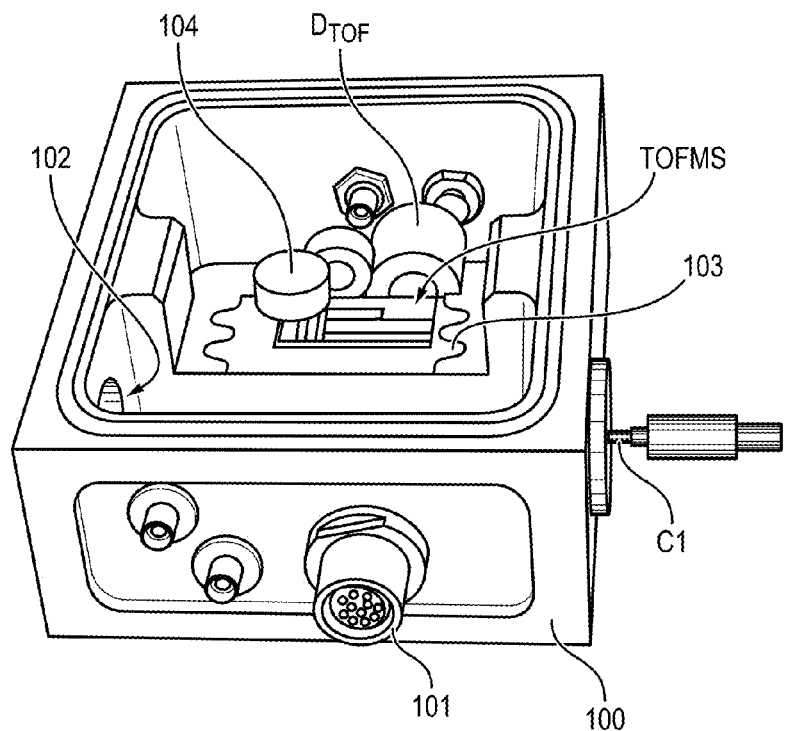
FIG. 12 is a perspective view of a case intended to receive the mass spectrometer in order to vacuum pressurise it.

Such a case 100 is shown open in FIG. 12, with the cover not shown.

A vacuum pump (not shown) is arranged for example on the outer wall of the case 100 and connected via a sealed passage 102 to the inner volume of the case.

The vacuum is indeed required for the proper operation of the ionization chamber, in order to ionise only the species to be analysed and no possible contaminants.

The vacuum furthermore makes it possible to increase the average free travel of the ions in the free-flight zone in order to preserve a transmission output that is as high as possible.

Note that the vacuum created in this miniaturised mass spectrometer does not require being as high (for example, limited to $10^{-3}$ mbar) as in most of the macroscopic mass spectrometers (which is of about $10^{-6}$ mbar).

Indeed, an absolute pressure of about $10^{-3}$ mbar is sufficient for implementing the analysis system according to the invention.

The vacuum pump is more preferably a miniature pump and can advantageously be chosen from among the following devices:
- a single primary pump of the ionic type, marketed for example by SAES, subject to an adaptation in order to optimise it with regards to the small volume of the mass spectrometer;
- the association of a small membrane primary pump, of the Pfeiffer MVP003 or MVP006 pump type, and of a miniature pump referred to as turbomolecular marketed by Creare, intended to refine the level of the vacuum or at least maintain it after each injection of species to be analysed in the micro-spectrometer.

It is also possible to position a valve between the outlet of the separation module and the inlet of the micro-spectrometer; this valve is actuated for the duration of each injection, which makes it possible to optimise the use of the pumps.

The case 100 further comprises a sealed passage 101 for the transmission cables for the input and output signals.

Advantageously, as said case 100 is typically made of a metal material, it constitutes a Faraday cage which makes it possible to isolate the mass spectrometer from outside electromagnetic disturbances.

The microcapillary tube C1 that connects the separation module (not shown) and the mass spectrometer enters the case 100 through a sealed passage.

The length of the various elements of the spectrometer depend on the characteristics that are to be given to the spectrometer.

The characteristic dimensions of this spectrometer can be close to 1 to 3 cm on the side for 1 to 1.5 mm in thickness.

This design of the micro-reflectron makes it possible to take advantage of the intrinsic performance of the architecture of time-of-flight mass spectrometers, namely a substantial range of analysed mass, good sensitivity, in particular due to the orthogonal injection, and the high-frequency mass spectrum acquisition.

As the final device is of small dimensions, the free average travel of the ions is substantially reduced in relation to that of a conventional mass spectrometer.

A method shall now be described that makes it possible to manufacture the mass spectrometer in the volume of a substrate by structuring the latter.

FIGS. 13A to 13K described hereinbelow correspond to a cross-section of the micro-reflectron R in a plane parallel to (y, z).

Although not shown in these figures, the other zones of the mass spectrometer were also formed during the steps of forming the micro-reflectron, by using the steps of structuring implemented, with the understanding that some elements (for example, the resistive layer of the micro-reflectron, or the various electrodes) may be formed only in particular regions of the mass spectrometer.

Figure 13A:
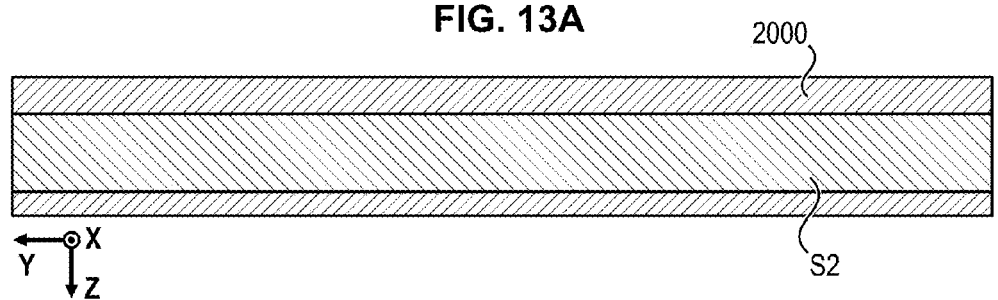
FIGS. 13A to 13K are cross-section views showing the steps of manufacturing the mass spectrometer.

In reference to FIG. 13A, a silicon substrate S2 is chosen which is covered over at least one of its main faces by a layer 2000 of a masking material that has a selectivity with regards to the etching in relation to silicon, with said layer 2000 intended to protect the regions of the substrate S2 which must not be etched.

For example, said masking layer 2000 is a layer of silicon oxide ($SiO_2$).

Its thickness is typically between 5 and 10 μm.

Said layer 2000 can be formed by thermal oxidation or via a deposition technique such as PECVD (Plasma-Enhanced Chemical Vapour Deposition).

Where applicable, a layer of the same material as that of the layer 2000 can also be formed on the other main face of the substrate S2, and can possibly be removed during a later step of manufacturing.

Figure 13B:
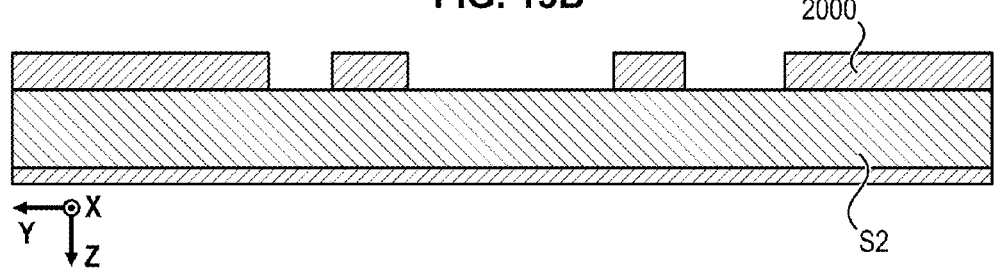

In reference to FIG. 13B, a step of dry etching (for example, etching of the RIE (Reactive Ion Etching) type of the masking layer 2000 is implemented in order to suppress the oxide of the regions of the surface of the substrate S2 which must be etched later.

Figure 13C:
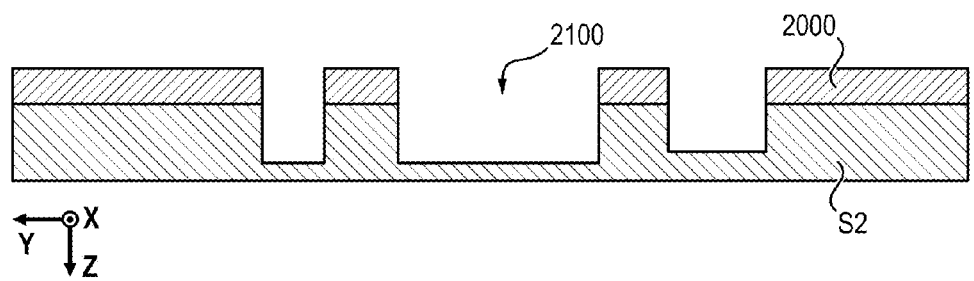

In reference to FIG. 13C, a step of deep etching is implemented, for example deep reactive ion etching) in order to avoid the substrate S2 with a view to forming the cavities intended for the passage of the ions in the spectrometer.

In the section considered, the cavity 2100 is as such intended to form walls of the micro-reflectron R.

Said etching is said to be deep as it is carried out at a depth of a few hundred micrometres.

In a later step not shown, the masking layer 2000 is removed, for example by means of hydrofluoric acid (HF).

Figure 13D:
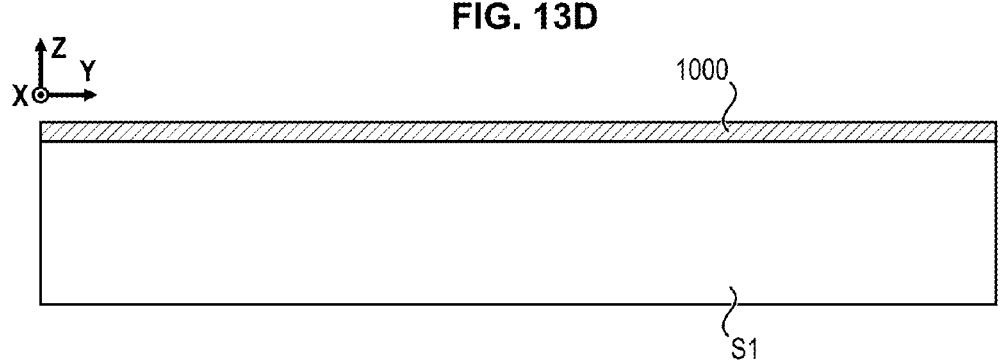

In reference to FIG. 13D, a glass substrate S1 is moreover used whereon a metal layer 1000 is deposited.

Said metal layer 1000 is intended to constitute the electrodes of the spectrometer.

Its thickness is about a few hundred nanometres, for example 500 nm.

Said layer 1000 is for example constituted of an aluminium-silicon alloy, of tungsten, of aluminium, or of titanium.

The metal layer 1000 can be deposited by any known technique, such as PVD (Physical Vapour Deposition) or an evaporation method.

Figure 13E:
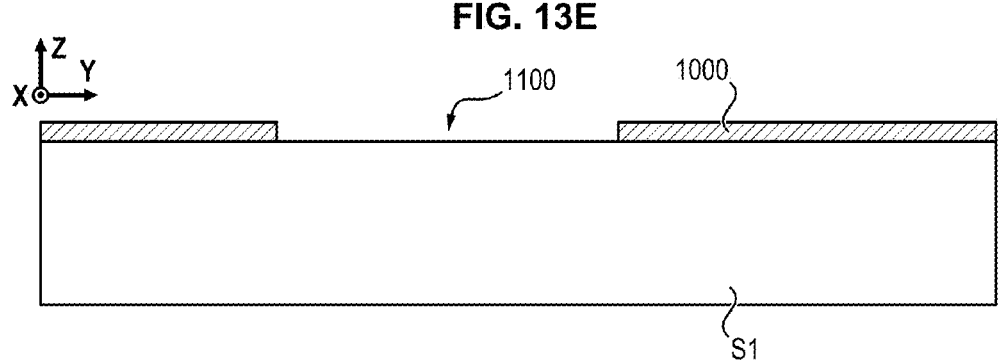

In reference to FIG. 13E, an etching of the metal layer 1000 is then implemented on certain regions of the substrate S1, in order to individualise the various electrodes of the mass spectrometer.

In particular, the region 1100 of the substrate S1 where the metal layer was removed 1000 corresponds to the region wherein the resistive wall of the micro-reflectron R1 must be deposited.

The etching can be carried out by wet processing, with an etching agent selected according to the metal of the metal layer 1000, or by plasma.

Figure 13F:
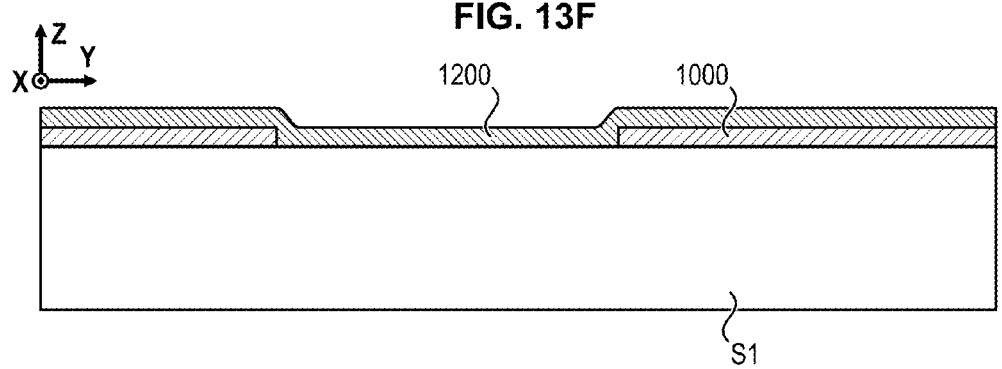

In reference to FIG. 13F, a layer 1200 of a resistive material is deposited intended to constitute the resistive layer of the micro-reflectron.

Said layer 1200 can be a semiconductor material such as amorphous silicon, polycrystalline silicon, germanium, and even a material other than a semiconductor.

The thickness of the layer 1200 depends on the electrical resistivity of the material chosen, in such a way as to generate, between the electrodes mentioned hereinabove, a potential gradient in the resistive layer of the micro-reflectron which is sufficient to create, in the micro-reflectron, an electrostatic field gradient that makes it possible to fulfil the function of deviation of ions In this respect, the thickness of the layer 1200 is typically between 5 and 500 nm.

Where applicable, the electrical resistivity of the layer 1200 can be adjusted via doping.

The deposit of the layer 1200 can be carried out example via epitaxy.

Figure 13G:
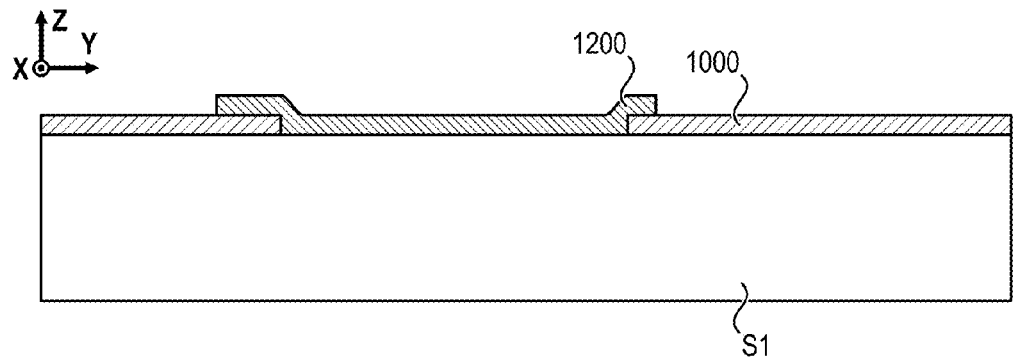

In reference to FIG. 13G, an etching of the resistive layer 1200 is then implemented in such a way as to remove it from all of the surface of the substrate S1 except in the region intended to form the wall of the micro-reflectron, by nevertheless maintaining direct contact between the resistive layer 1200 and the underlying metal layer 1000 in such a way as to allow for the polarisation of the resistive layer using electrodes formed using the metal layer.

In this zone of contact, the resistive layer is locally doped in order to provide good ohmic contact.

The etching can be a dry etching by plasma or wet etching.

Figure 13H:
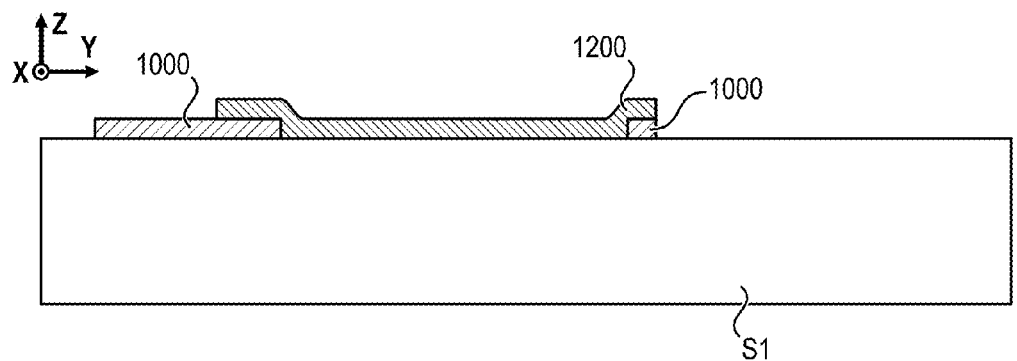

Finally, in reference to FIG. 13H, a last series of etching steps of the metal layer 1000 and of the resistive layer 1200 can be implemented in order to define the shape of the electrodes.

Advantageously, the metal layer 1000 laterally exceeds the resistive layer 1200, which makes it possible to facilitate the polarisation of the electrode.

Figure 13I:
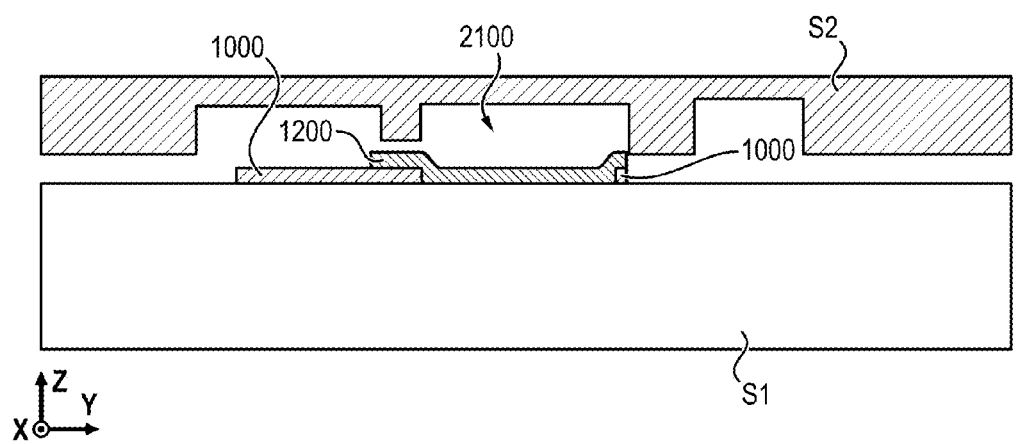

Then, in reference to FIG. 13I, the substrate S1 and the substrate S2 are made integral.

Advantageously, the technique for rendering integral said substrates is the anodic bonding technique, which, via compression, heating and polarisation of the silicon/glass unit, induces chemical bonds on the interface between the glass of the substrate S1 and the silicon of the substrate S2.

For example, the temperature for implementing this technique is about 500° C. and the polarisation voltage is about 1 kV.

Figure 13J:
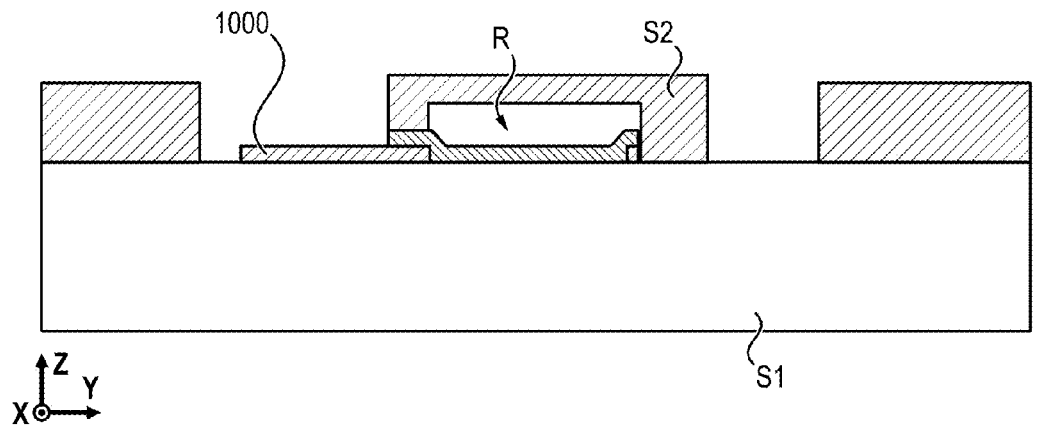

Alternatively, the making integral of the substrates can be carried out by a bonding by means of a resin, or eutectic gluing, of the tin-lead, gold-tin, etc. type In reference to FIG. 13J, the silicon substrate S2 is etched again through a mask (not shown).

This etching makes it possible to individualise the channel wherein the ions are going to travel and, where applicable, complete the structuring of the other parts of the spectrometer.

As such, for example, the lenses L1 to L3 of the focussing zone MS2 can be structured in the silicon substrate S2 in the form of silicon rings separated by a distance of about 1 mm.

It can be observed that, in the flight channel formed as such, the electrode located under the resistive layer 1200 remains accessible from the outside of the channel, the resistive layer 1200 being on the contrary enclosed in the volume of the channel.

Figure 13K:
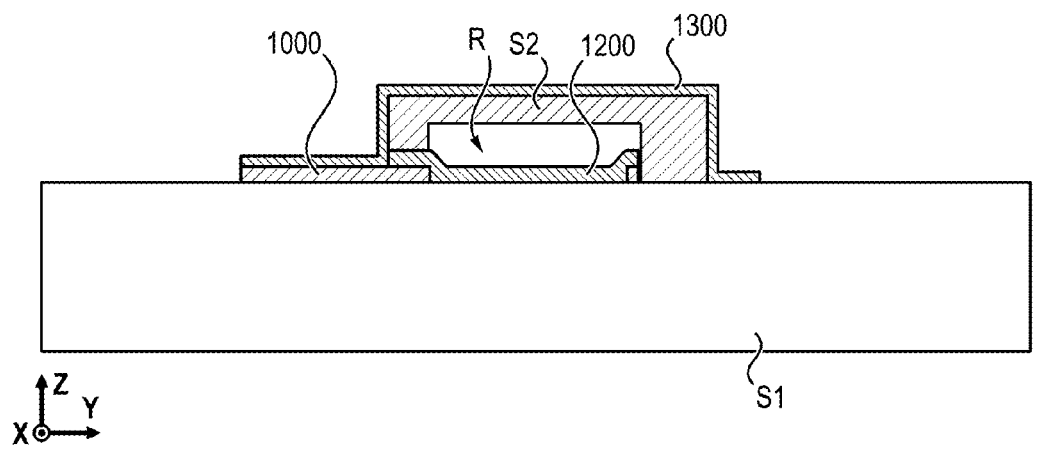

Then, in reference to FIG. 13K, another deposit of a metal layer 1300 is implemented intended to form an electrode surrounding the entire section of the channel.

A micro-time-of-flight mass spectrometer is as such obtained formed monolithically in the volume of the substrates S1 and S2, with the substrate S1 also fulfilling the support function of the device.

According to an embodiment, the chromatography column and the mass spectrometer are each made on a silicon chip according to the methods described hereinabove.

They can then be connected by a microcapillary tube of deactivated silica, which does not generate any chemical interaction between the species of the sample and the walls of said microcapillary tube.

Alternatively, it is also possible to connect the column and the mass spectrometer by superimposing two substrates or two chips bearing these devices.

Figure 14:
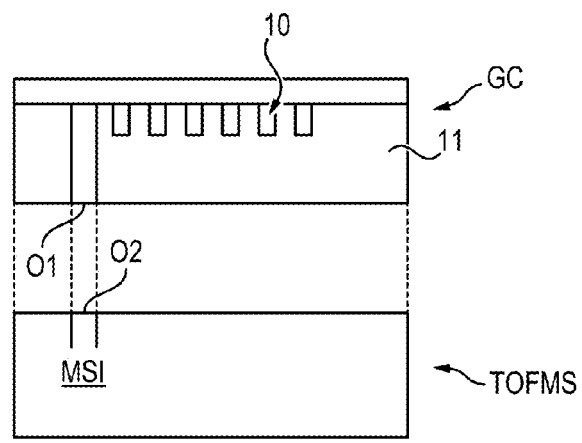
FIG. 14 is a cross-section view that shows the principle of the stacking of a substrate bearing a mass spectrometer and of a substrate bearing a microcapillary chromatography column.

As shown as a diagrammatical cross-section in FIG. 14, this supposes having carried out beforehand, in the substrate comprising the microcapillary column GC, an opening O1 passing through a main face of said substrate in order to allow the outlet of the effluent in a direction perpendicular to said face, and, in the substrate comprising the mass spectrometer TOFMS, an opening O2 passing through a main face of said substrate in order to allow for the inlet of the effluent of the column in the ionization chamber of the mass spectrometer.

An alignment of the substrates makes it possible to provide a putting into correspondence of these openings O1, O2 during the assembly.

A chip can then be individualised by cutting said assembled substrates.

A three-dimensional device is as such formed comprising a stage of separation and a stage of mass spectrometry.

Finally, it can also be considered to integrate, on the same silicon chip, the chromatography column and the mass spectrometer.

This embodiment is described in detail hereinbelow.

Figure 15A:
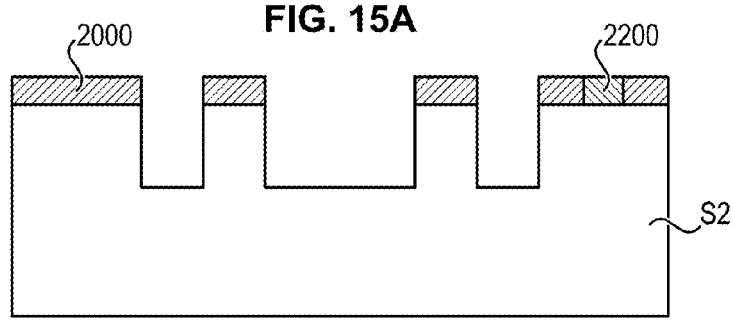
FIGS. 15A to 15C are cross-section view showing the steps of manufacturing the mass spectrometer and a microcapillary chromatography column in the volume of the same substrate.
Figure 15B:
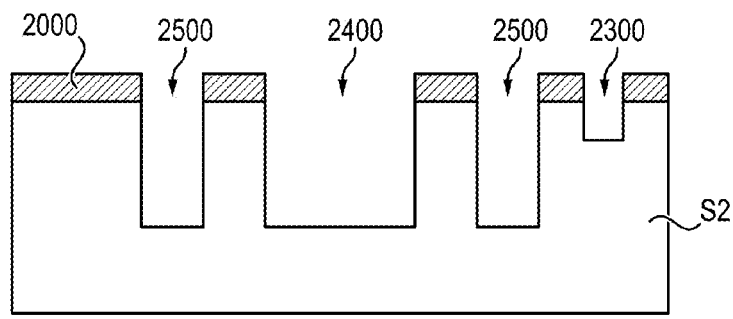
Figure 15C:
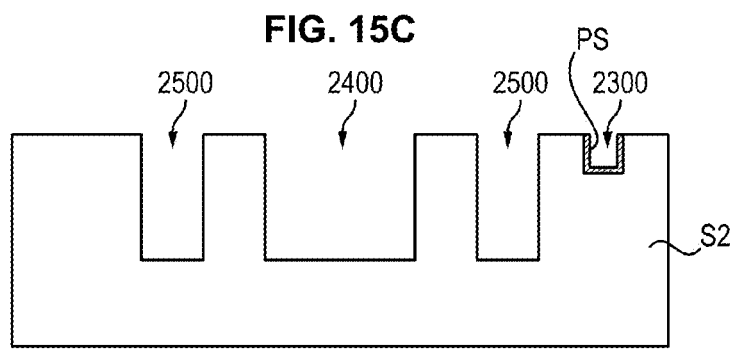

Integration of the Microcapillary Chromatography Column and of the Mass Spectrometer on the Same Silicon Chip FIGS. 15A to 15C are cross-section views according to a cut plane similar to that of FIGS. 13A to 13K.

In reference to FIG. 15A, a silicon substrate S2 is chosen in order to structure therein the walls of the channel wherein the ions circulate in the mass spectrometer.

Two etching masks 2000, 2200 are formed on said substrate S2.

A portion of the first mask 2000 is etched corresponding to the regions of the substrate S2 to be etched in order to form the elements of the mass spectrometer, the deep reactive ionic etching of the substrate S2 is then implemented in order to form the cavities required for structuring the mass spectrometer.

In reference to FIG. 15B, the second masque 2200 is etched corresponding to the regions of the substrate S2 to be etched in order to form the groove of the microcapillary chromatography column, then said groove 2300 is etched in the substrate S2 by continuing the deep reactive ionic etching.

Said groove 2300 can for example have the form of a spiral such as shown in FIGS. 6 and 7.

After these two sequences of deep reactive ionic etching, the silicon substrate therefore comprises cavities 2400 belonging to the mass spectrometer, and which have a depth of about 600 μm, while the groove 2300 of the chromatography column has a depth of about 100 μm (cf. FIG. 15C). The cavities 2500 that can be seen on either side of the cavity 2400 make it possible to access the channel which will be formed after the substrate S2 is made integral with the glass substrate S1, in order to make the electrodes.

In reference to FIG. 15C, the groove 2300 of the chromatography column is functionalised by depositing therein the stationary phase PS selected.

Said stationary phase can be deposited locally only in said groove 2300, by using stencilling or lithography techniques.

Alternatively, it can be considered to deposit the stationary phase over the entire surface of the substrate S2 by using techniques such as sputtering, physical vapour deposition (PVD).

In this case, the walls of the channel wherein the ions will circulate in the mass spectrometer are then also covered by the stationary phase.

This coating does not disturb however the electrostatic control of the ions as long as the stationary phase has dielectric properties, which is the case of phases such as porous silica, silicon oxide doped with carbon (SiOC), etc.

By this method, it is possible to collectively manufacture, on a substrate with a diameter of 200 mm for example, a plurality of micro-spectrometers and columns, then to individualise the chips by cutting the substrate.

The later steps are identical to those described in reference to FIGS. 13D to 13K, i.e. the substrate S2 structured as such is made integral with a substrate S1 whereon have been formed electrodes of the mass spectrometer as well as the resistive layer of the micro-reflectron, then an additional etching is carried out of the substrate S2 (in particular on cavities 2500) in order to access the walls of the circulation channel of the ions and form the electrodes that surround said channel.

Non-destructive Micro or Nano-detector

Advantageously but optionally, the system further comprises at least one non-destructive micro or nano-detector.

This type of detector comprises electromagnetic detectors of the MEMS, NEMS or non-electromechanical types, such as the nano-TCD.

These detectors have the advantage of taking a non-destructive measurement, in such a way that they can be placed upstream of the mass spectrometer.

On the contrary, as the mass spectrometer carries out a destructive measurement, it would not indeed be possible to place such detectors downstream of the mass spectrometer.

As explained hereinabove, the choice of the detector must take into account the possibility of setting it into place in the fluidic stream wherein the gas circulates without affecting the regularity of the cross section of said stream.

The combination of at least one micro or nano-detector and of the time-of-flight mass spectrometer has several advantages.

On the one hand, it makes it possible to procure a self-diagnostic function of the system.

Indeed, the fact that one of the devices detects a species while the other does not detect it is a hint that there is a malfunction in the system.

Likewise, a calibration of the system is made possible by the injection of a reference sample that has a known composition; the coherence of the results obtained by each one of the two devices then makes it possible to confirm the proper operation of the non-destructive micro or nano-detector and of the mass spectrometer.

On the other hand, this combination makes it possible to refine the information collected on the various species present in the sample.

Indeed, wherein the micro or nano-detector and the mass spectrometer are based on different measurement principles, the information obtained by each one of these devices is complementary and make it possible, where applicable, to discriminate two species that are not differentiated by one of the devices used independently.

Such is the case in particular when the sample contains several species that have the same mass/charge (m/z) ratio, due to the very nature of these species or of a strong ionisation that has for effect to load in a multiple way a species or to break it.

For example, the molecules $CH_3CHOH$, $CH_2CH_2OH$ and $CH_2OCH_2$ have an identical ratio m/z equal to 45; the molecules CN (cyanide) and $C_2H_2$ have an identical ratio m/z equal to 26.

These molecules are therefore difficult to differentiate by the mass spectrometer, without appropriate signal treatment.

On the other hand, these molecules can be differentiated directly by their chemical affinity with a functionalising layer deposited on a gravimetric detector of the MEMS or NEMS type.

Furthermore, when a particular species must be detected by the analysis system, it is possible to functionalise the nano or micro-detector with a very selective material and which reacts specifically to the presence of this species.

This makes it possible to reduce the detection of false positives or false negatives.

This embodiment therefore has a particular interest for the control of a toxic species on an industrial site, or for monitoring the exposure to a neurotoxin chemical agent (CWA, or "Chemical Warfare Agent").

Moreover, one or several NEMS detectors of the resonator type can be advantageously placed as close as possible to the mass spectrometer, in the vacuum pressurised case wherein it is housed, in order to improve the performance of the NEMS detectors.

Indeed, the quality factor for these nano-structures is improved by about a factor of 10 at the pressures under consideration, which makes it possible to lower the detection thresholds.

Finally, according to an embodiment described in the example no. 1, it is possible to integrate at least one micro or nano-detector to at least one microcapillary chromatography column, such as is described in document WO 2011/154362.

Complete Analysis System

As the main components of the analysis system have been described individually, their assembly in order to form a functional device is disclosed briefly hereinbelow.

In addition to these main components, whether or not optional, the analysis system further comprises an electronic control board for each component (microcontroller for managing injections, the separation module, valves, the heating modules if needed, etc.) and an electronic control board for the detection portion (electronic board for the mass spectrometer portion, additional electronic lo board for the NEMS portion where applicable).

To this can be added a pump that makes it possible to sample the samples of interest in certain cases (in the ambient air for example or elsewhere), power supplies (for electronic boards, thermalisation modules, sources of ionisation, detectors, etc.) and an external connection card (Ethernet card for example) in order to recover the data.

Wireless transmission modules (for wifi or Bluetooth, etc. connections, for example with portable computers, tablets, etc.) can also be added.

The unit is placed in a case (typically the size of a shoebox) of which the volume can be 1 litre for a weight of about 1 kg.

EXAMPLE NO. 1

Coupling the Mass Spectrometer to a Microcapillary Chromatography Column Instrumented with Micro or Nano-detectors According to an embodiment, the analysis system further comprises at least one micro or nano-detector placed upstream of the mass spectrometer.

According to an embodiment, said detector is inserted between the outlet of the separation module and the inlet of the mass spectrometer.

According to another embodiment, said detector is arranged inside a microcapillary chromatography column, more preferably incorporated into the wall of the latter.

The integration of a detector in a chromatography column carried out in a silicon chip is described in [11].

According to a preferred embodiment, on the one hand the groove defining the chromatography column is etched in a first substrate.

On the other hand, a plurality of micro or nano-detectors is formed in a second substrate distributed according to a pattern that corresponds to the path of the groove.

The second substrate is assembled on the first one by bonding of the molecular, eutectic, anodic, dry film (resin) or silkscreen type, in such a way as to put the groove into correspondence with the various detectors.

It is also possible to combine these two embodiments by arranging in the system at least one detector in a microcapillary chromatography column and a detector at the outlet of said column, outside of the latter. This makes it possible to use more easily detectors functionalised by different substances of the stationary phase.

Figure 17:
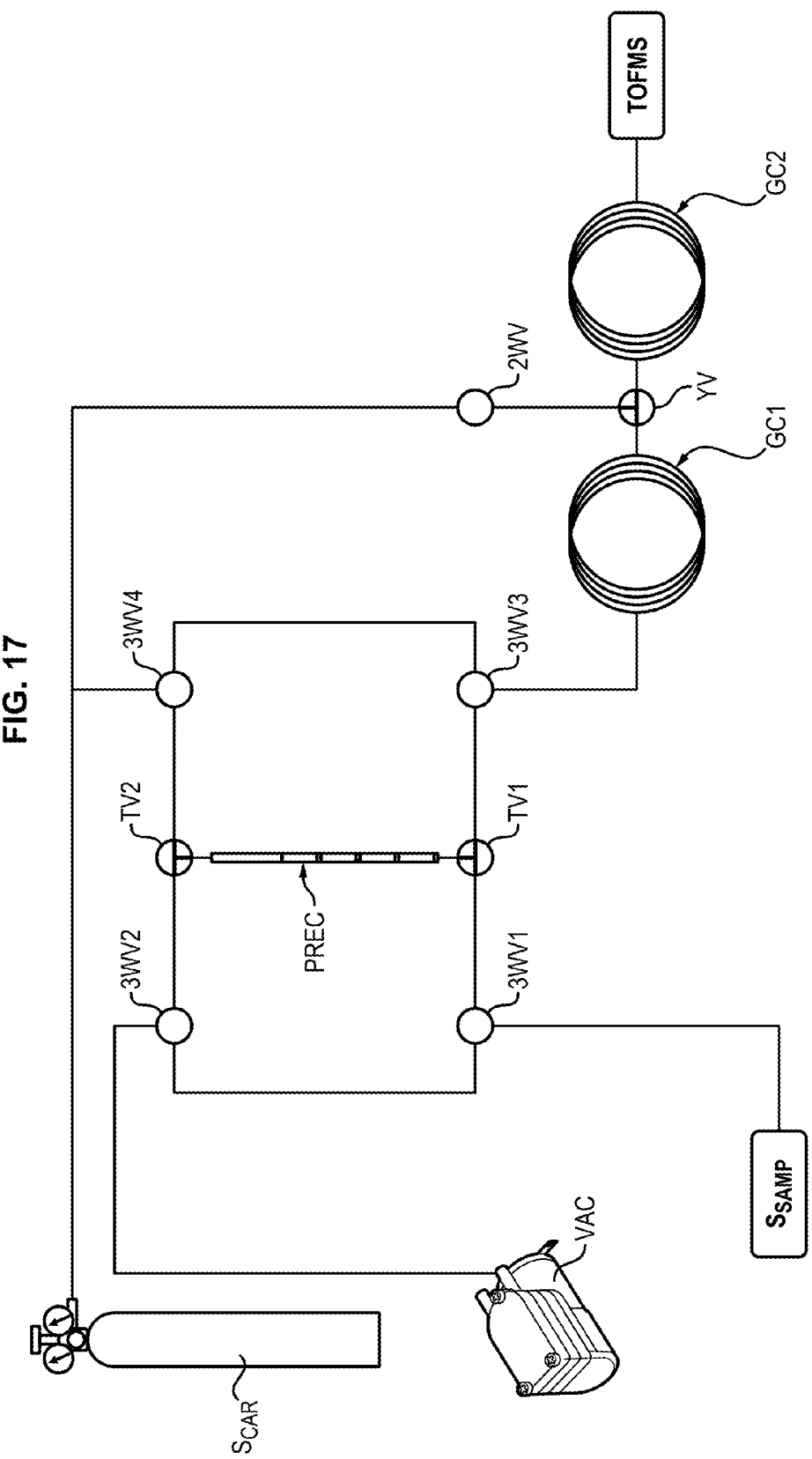
FIG. 17 is a diagram of an embodiment of the preconcentration and modulation circuit, in the case where the separation module comprises two microcapillary gas phase chromatography columns (GC×GC)

Particularly advantageously, a plurality of detectors $DNEMS_i$ (where i is an integer between 2 and the total number of detectors) are arranged from the inlet of the column to the outlet of the column, with the detectors being regularly spaced and of a sufficient number so that their separation is less than half of the width of a peak (FIG. 17).

Thanks to the presence of this plurality of gas detectors, it is possible to follow the displacement of species within the column and to more precisely estimate the instantaneous speed.

For a given column, the average width of a peak can be estimated by the "equivalent height at a theoretical stage".

In practice, it is advantageous to have detectors spaced about a millimetre environ, or about 1000 for a one-metre column.

The detectors are chosen in such a way that their size makes it possible to arrange them inside the column.

In the case of a microcapillary chromatography column, the typical cross section of such as column has a width of a few tens of micrometres, the elementary detectors chosen thus have a size less than this value.

As such, a nano-detector can have a useful surface of a few 100 $nm^2$ to a few $\mu m^2$ according to the diameter of the column.

Preferably, the detectors are as small as possible, which makes it possible to increase the sensitivity of the means for detecting and the number of detectors.

This is the case in particular of NEMS of which at least one of the lateral dimensions is less than the micrometre.

It is even possible to carry out an elementary detector by several juxtaposed NEMS.

NEMS detectors are for example gravimetric NEMS sensors such as those described in [9], [12] or [13].

The sensors are advantageously functionalised with a sensitive polymer, or any other absorbent material that has a chemical affinity with the species of the mixture to be analysed. In the presence of a chemical species, a certain quantity of this species will be adsorbed on the sensitive layer and generate a signal on the sensor. The adsorbent material can be identical to the stationary phase or be different.

It is of course understood that an elementary detector can be formed from several NEMS micro or nano-sensors.

The detectors can possibly include other micro-sensors or nano-sensors for known gases, in particular conductimetric sensors, wherein the deposit of molecules on a support is accompanied by a change in the electrical conductivity. Said support can be constituted of carbon nanotubes.

The detectors can also include detectors referred to as nano-TCD (Thermal Conductivity Detector) which measure the variation in the thermal conductivity of the sample of gas when the latter passes on the sensor in relation to that of a reference bearing gas.

Thanks to said micro or nano-detectors arranged in the microcapillary column, it is possible to carry out analyses with a rate that is higher than in prior art.

Indeed, it is no longer necessary to wait for all of the species from a preceding sample to have exited the column before injecting the next sample, since each one of the species is followed during its displacement in the column and is no longer detected solely at the outlet.

EXAMPLE NO. 2

Coupling of the Mass Spectrometer with a Two-Dimensional Chromatographic Separation Module (GC×GC)

According to an embodiment, the separation module can comprise more than one microcapillary chromatography column.

As such, according to an advantageous embodiment shown in FIG. 17, the module comprises two microcapillary columns for chromatography GC1, GC2 having different degrees of selectivity.

The lengths of said columns can also be different; as such, advantageously, the second column is shorter than the first one.

These two columns, which are connected in series, have the advantage of increasing the resolution of the step of separation and the capacity of peaks.

The different degrees of selectivity are typically procured by different stationary phases.

As such, for example, the stationary phase of the first column is a non-polar phase, such as polydimethylsiloxane (PDMS).

The stationary phase of the second column can be a polar phase, such as polyethylene glycol (PEG).

Naturally, those skilled in the art may need to choose other stationary phases in order to optimiser the separation of the various species present in the sample.

Such an association of two columns is described in [9].

In this article, the two columns are furthermore associated with a NEMS detector; however, even if the use of such a detector is advantageous, the analysis system can include these two columns without any detector, a flow modulator then being coupled to said columns in order to manage the flow of gas successively through each one of the columns.

The function of the modulator is to allow for the separation in the first column GC1, the to freeze the flow in said first column during the passage of the effluent collected in the second column GC2.

The modulator therefore acts sequentially, with the duration of the separation along the second column GC2 being designated by the term of modulation period.

The modulation period can thus be broken down into a first phase corresponding to the duration of the transfer of the effluent of the first column to the second column, and a second phase of separation of said effluent par the second column.

According to an embodiment, the modulator is a modulator of the "stop-flow" type.

Such a modulator is described for example in [10].

The modulator comprises a valve YV which is a Y-shaped valve, without dead volume, arranged between the first and the second column.

Zero dead volume Y-shaped valves treated by Sulfinert™ are available from Restek under the reference 21389.

The modulator further comprises a valve 2WV, which is a normally-open 2-way valve, which is arranged between the source $S_{CAR}$ of carrier gas and the Y-shaped valve YV.

Figure 18:
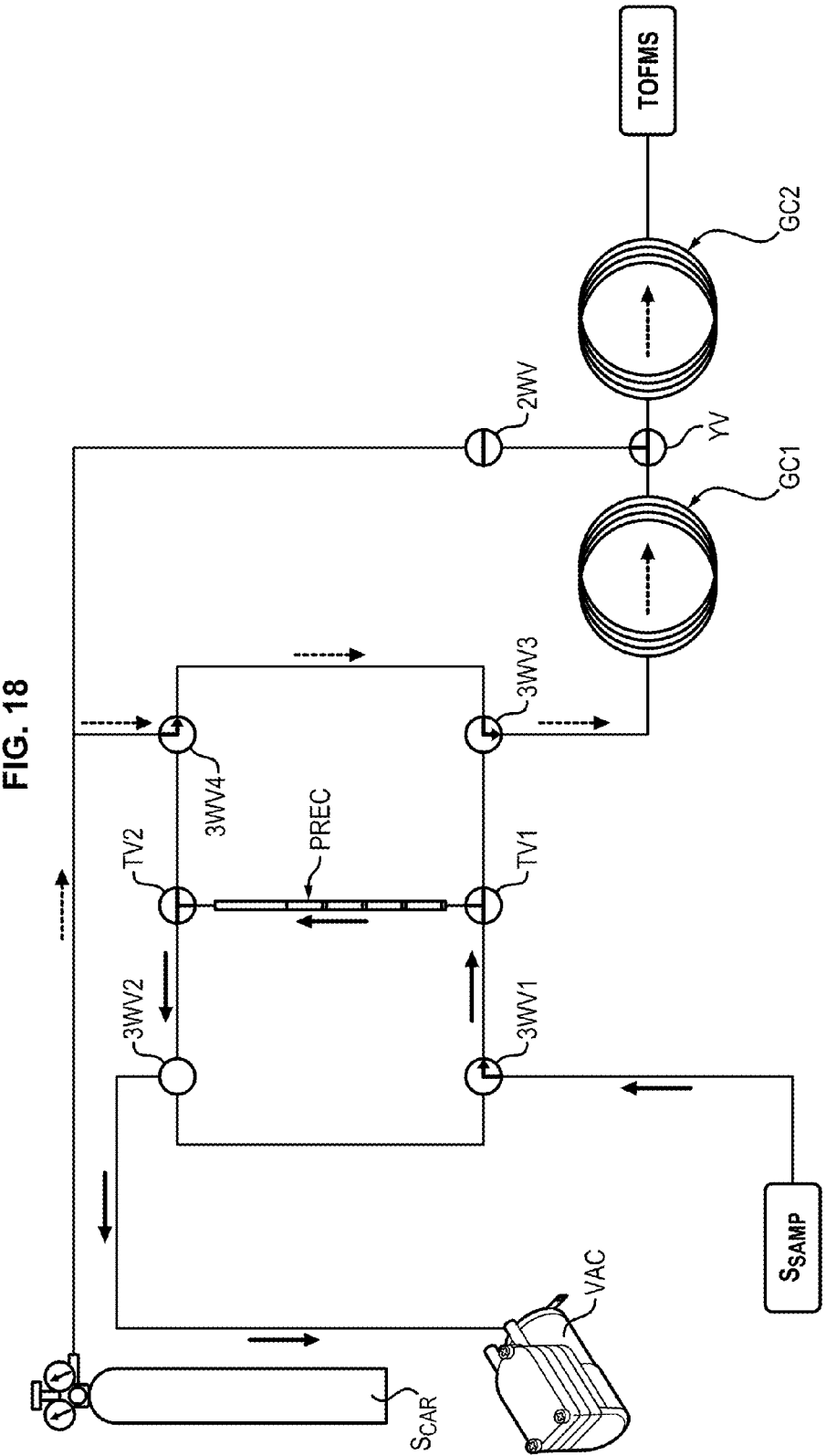
FIG. 18 shows, based on FIG. 17, the circulation of the gaseous sample with a view to the adsorption of its various species in the preconcentrator.
Figure 19:
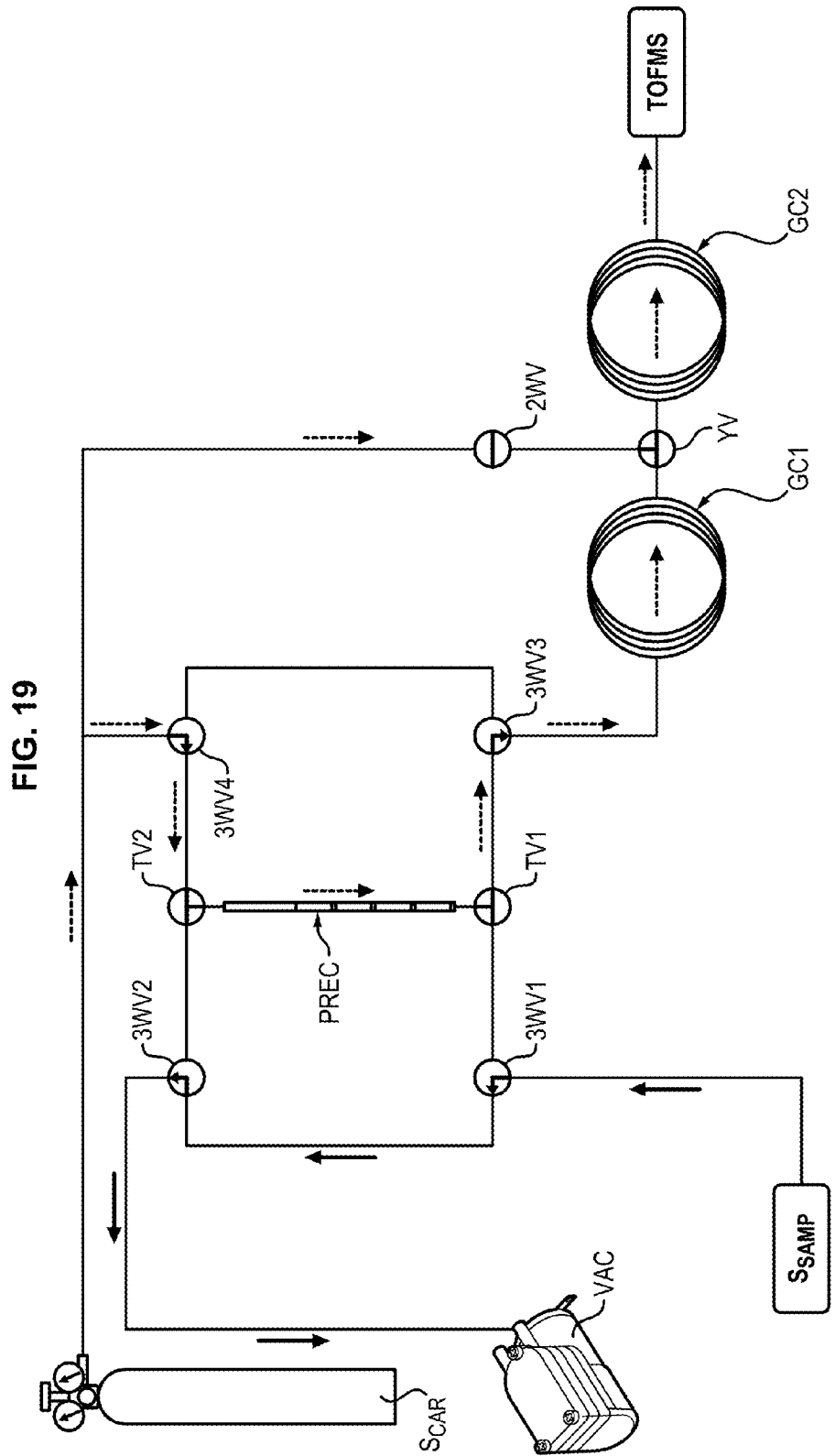
FIG. 19 shows, based on FIG. 17, the circulation of the carrier gas with a view to the desorption of the species adsorbed beforehand and the passage in the first chromatography column (first modulation phase, referred to as loading phase of the second dimension)
Figure 20:
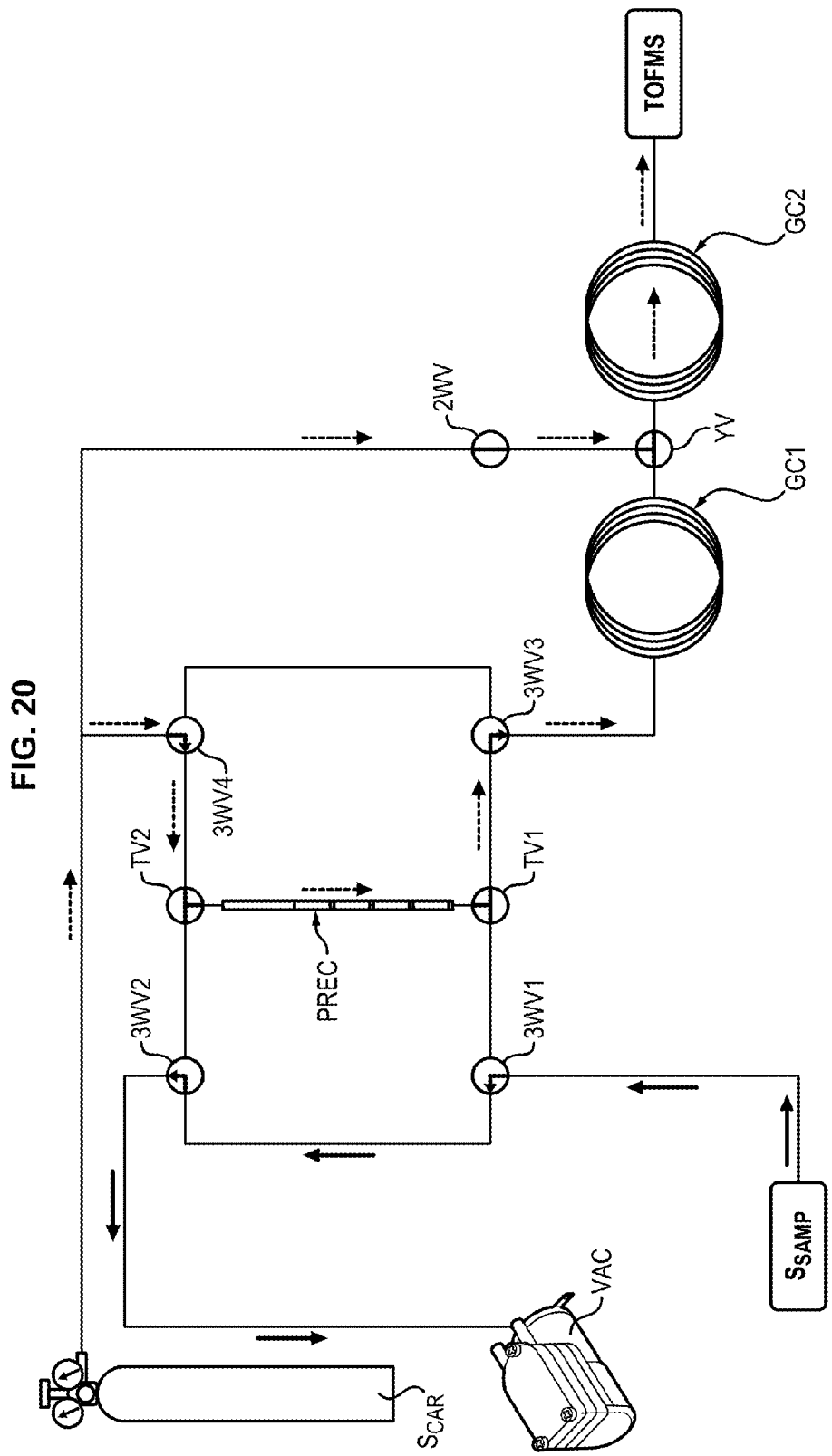
FIG. 20 shows, based on FIG. 17, the circulation of the carrier gas with a view to the passing in the second chromatography column (second modulation phase, referred to as analysis phase of the second dimension)

FIGS. 18 to 20 show the various operating sequences of the modulator and of the separation by the two associated columns.

The valves that have the same reference signs as in FIG. 3 have already been described in reference to this figure and shall not be described again here.

In reference to FIG. 18, and as in the case shown in FIG. 4, said valves are at first controlled in order to allow for the passage of the sample in the preconcentrator so that its species are adsorbed therein, while the carrier gas circulates, isolated from the sample, through the first then the second column, until the mass spectrometer. The valve 2WV is closed during this phase.

This phase is implemented only when a preconcentration is required.

During the first phase of the modulation period, referred to as loading phase of the second dimension, shown in FIG. 19, the valve 2WV connecting the valve YV arranged between the two columns and the source of carrier gas is closed, while the valve YV is open, in such a way that the carrier gas driven by desorption the species trapped in the preconcentrator PREC through the first column GC1 then the second column GC2. The carrier gas is however blocked by the closed valve 2VW and therefore cannot directly pass through the second column.

During the second phase of the modulation period, referred to as analysis phase of the second dimension, shown in FIG. 20, the valve 2WV connecting the valve YV arranged between the two columns and the source of carrier gas is open, the valve YV also being open.

Due to the opening of the valve 2WV, which allows for the passing of the carrier gas to the valve YV, the pressure at the junction between the two columns increases in order to reach the pressure at the inlet of the first column.

This increase in pressure has the following consequences:
in the absence of a difference in pressure allowing for the flow of the carrier gas in the first column, the flow is frozen in the first column;
due to the increase in the difference in pressure between the inlet and the outlet of the second column, the flow of gas circulates in the second column and allows for a fast separation of the effluent from the first column which was introduced therein.

The duration of this second phase of the modulation period must be sufficient in order to guarantee that the species retained the longest amount of time in the second column has completely exited therefrom before closing the valve located at the junction between the two columns and to initiate another transfer of the effluent from the first column to the second.

Typically, in a modulator of the "stop-flow" type, the duration of the loading phase is about 0.1 to 1 second while the duration of the analysis phase that follows it is about 0.5 to 4 seconds.

The modulation period is equal to the sum of the durations of these two phases.

However, these values are able to change according to the application, the type of columns and conditions for implementing the separation.

Note that the invention is not limited to a modulator of the "stop-flow" type but that other existing modulators can be used in the analysis system.

Among the types of known modulators, thermal modulators, valve modulators and differential flow modulators can be mentioned.

Moreover, the operation of the modulator was described here in relation with the implementation of a preconcentration.

However, as indicated hereinabove, the preconcentration is optional and the modulator can operate according to the same principle as that described hereinabove without the system comprising a preconcentrator.

Figure 16:
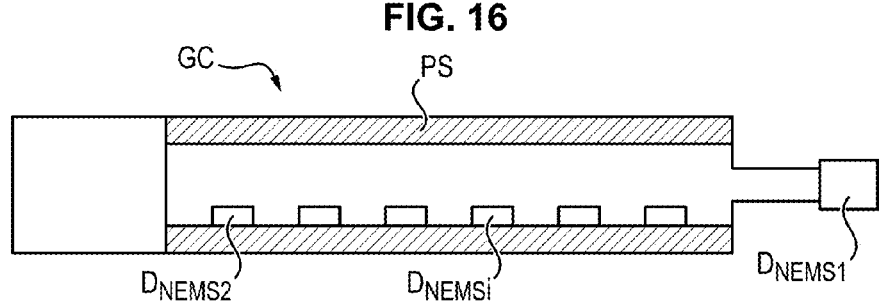
FIG. 16 is a cross-section view of a microcapillary chromatography column wherein several detectors of the NEMS type are arranged.

According to another embodiment of the invention, it is possible to advantageously arrange, in each one of the columns, a plurality of micro or nano-detectors such as described in the example no. 1 and diagrammed in FIG. 16.

Said detectors make it possible to overcome the modulator described hereinabove.

Indeed, it is no longer useful to freeze the flow coming from the first column the time of the separation in the second column since the integration of said detectors makes it possible to obtain an image in real time of the formation of the peaks in each one of the columns and therefore to follow the history perfectly (even in the case of peaks that overlap or combine together, etc.).

It thus becomes possible to couple more than two columns in series (up to five, for example) with different stationary phases in order to multiply the dimensions of separation and analyse potentially complex mixtures (i.e. comprising several hundred to several thousand separate species).

The integration of said micro or nano-detectors implies manufacturing the microcapillary columns in silicon substrates, depending on the etching method then depositing the stationary phase described hereinabove.

On the other hand, if it is chosen to manage the flow of gas in the columns by using a modulator, said columns can be either microcapillary tubes or columns arranged in the volume of a silicon substrate.

The association of the two columns is known under the term of comprehensive two-dimensional chromatography (noted as "GC×GC") as the entire amount of a sample which is introduced at the inlet of the first column is introduced into the detector (namely the mass spectrometer or, where applicable, in a NEMS detector placed upstream of the latter) at the outlet of the second column, without loss of a portion of the sample.

The two-dimensional nature of the chromatographic separation is linked to the fact that the two stationary phases are different and chosen in such a way as to present separation mechanisms that are as independent from one another as possible.

As such, the first and second columns can be considered as respectively representing a first and a second dimension of separation.

Figure 21:
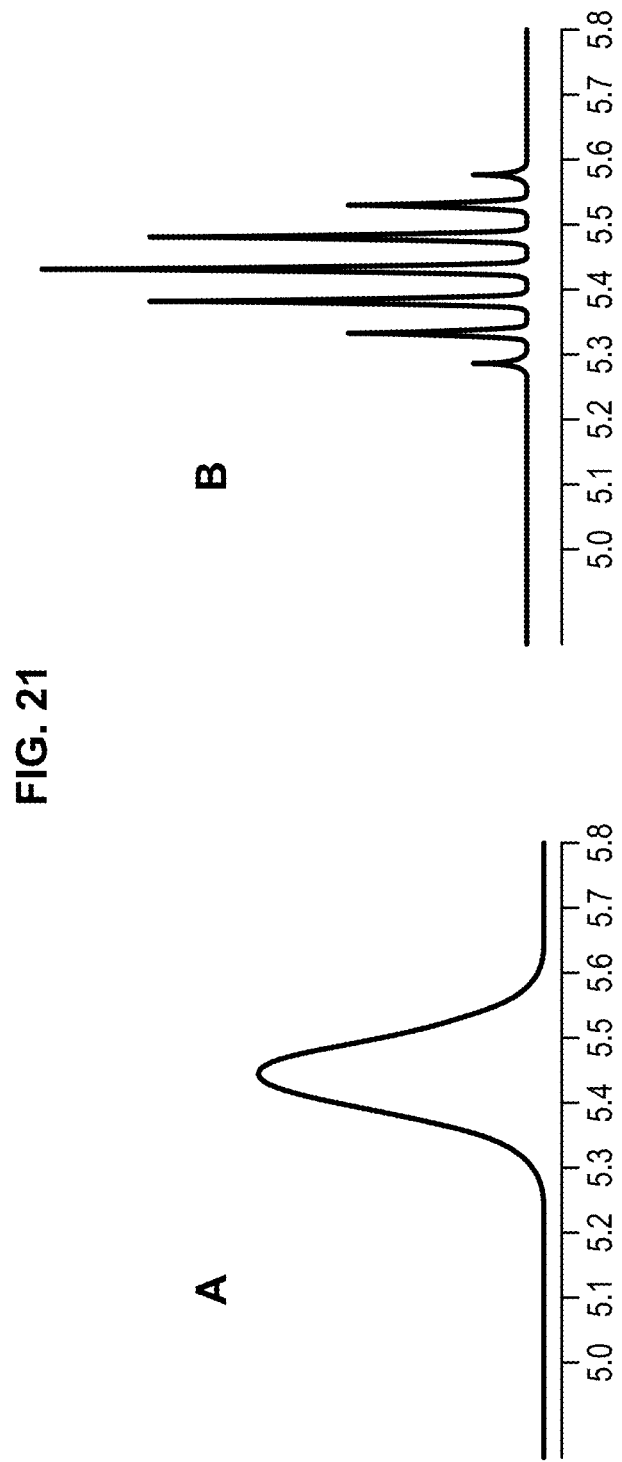
FIG. 21 shows the peaks obtained respectively at the outlet of the first chromatography column (curve A) and at the outlet of the two columns coupled by the modulator (curve B).

FIG. 21 shows the peaks obtained respectively at the outlet of the first column GC1 utilised in isolation (curve A) and at the outlet of the two columns GC1 and GC2 jointly (curve B).

It appears clearly that in the first case the separation results in a single peak which is relatively large, while in the second case the separation results in a plurality of narrower peaks, which are included in the initial peak and which each correspond to a modulation period.

Indeed, thanks to its stationary phase independent of that of the first column, the second column is able to separate species which, in the first column, have the lo same retention time.

Naturally, the separation module can include more than two microcapillary columns for chromatography that have different degrees of selectivity and coupled in series by modulators and/or instrumented by micro or nano-detectors without however leaving the scope of this invention. It is therefore possible to speak of multi-dimensional chromatography.

The coupling of such a series of columns with the mass spectrometer makes it possible as such to carry out a multidimensional separation module with an ultra compact mass spectrometer.

It is naturally possible to combine the various embodiments described hereinabove.

The analysis system can be used for the detection of pollutants or toxic compounds.

Due to its small size and its low energy consumption, it can be presented in the form of a portable and autonomous device, able to be transported by an operator with the view to carry out measurement in the field.

The analysis system can also be used for biomedical analysis, for example in order to identify biomarkers, with the sample then being a bodily gas such as breath.

The analysis system can also be used for the monitoring of manufacturing lines and agro-food distribution.

Finally, it goes without saying that the examples that have just been given are simply particular illustrations and in no way limitative as to the scope of the invention.

REFERENCES

[1] E. Wapelhorst, J. P. Hauschild, J. Müller, 'Complex MEMS: a fully integrated TOF micro mass spectrometer', Sensors and Actuators A 138 (2007) 22-27

[2] P. Siebert, G. Petzold, A. Hellenbart, J. Müller, 'Surface microstructure/miniature mass spectrometer', Applied Physics, A67, 155-160 (1998)

[3] H. J. Yoon, J. H. Kim, E. S. Choi, S. S. Yang, K. W. Jung, 'Fabrication of a novel micro time-of-flight mass spectrometer', Sensors and Actuators A 97-98 (2002) 441-447

[4] J. P. Hauschild, E. Wapelhorst, J. Muller, 'Mass spectra measured by a fully integrated MEMS mass spectrometer', International Journal of Mass Spectrometry 264 (2007) 53-60

[5] C. Lu, E. Zellers, Anal. Chem. 2001, 73, 3449

[6] C. Lu, E. Zellers, Analyst 2002, 127, 1061

[7] J. M. Sanchez, R. D. Sacks, Anal. Chem. 2003, 75, 978

[8] J. M. Sanchez, R. D. Sacks, Anal. Chem. 2003, 75, 2231

[9] J. J. Whiting, C. S. Fix, J. M. Anderson, A. W. Staton, R. P. Manginell, D. R. Wheeler, E. B. Myers, M. L. Roukes, R. J. Simonson, 'High-speed two-dimensional gas chromatography using microfabricated GC columns combined with nanoelectromechanical mass sensors', Transducers 2009, 1666-1669

[10] C. S. Fix, J. J. Whiting, D. Porter, D. Graf, R. P. Manginell, J. M. Anderson, C. Washburn, A. Staton, S. Howell, J. Richards, E. Myers, M. Roukes, R. J. Simonson, 'A high-speed two dimensional gas chromatography using micro fabricated GC columns combined with nanoelectromechanical mass sensors', Solid-State Sensors, Actuators and Microsystems Conference, 2009. TRANSDUCERS 2009. International—10.1109/SENSOR.2009.5285751

[11] WO 2011/154362

[12] EP 2 211 185

[13] E. Mile, G. Jourdan, I. Bargatin, S. Labarthe, C. Marcoux, P. Andreucci, S. Hentz, C. Kharrat, E. Colinet and L. Duraffourg, 'In-plane nanoelectromechanical resonators based on silicon nanowire piezoresistive detection', Nanotechnology 21 (2010) 165504

The invention claimed is:

1. A gas analysis system comprising, from upstream to downstream:
   a module for separating at least a portion of the species contained in the gas to be analysed, comprising at least one microcapillary gas phase chromatography column, and
   a time-of-flight mass spectrometer coupled to said separation module, said spectrometer comprising a source of ions adapted to ionise at least a portion of said species and to emit a beam of ions, and a free-flight zone for said ions,
   said mass spectrometer being arranged in the volume of at least one substrate and comprising a micro-reflectron arranged between the source of ions and the free-flight zone, a wall of said micro-reflectron comprising a layer made from a resistive material designed to be polarised between at least two regions of said layer in such a way as to create a continuous electrostatic field gradient in order to deviate the trajectory of the ions in said micro-reflectron.

2. The system of claim 1, wherein the micro-reflectron is arranged in such a way as to be passed through by the ions in a longitudinal direction parallel to the direction of the beam of ions at the outlet of the source and the resistive layer is designed to be polarised in such a way that the continuous electrostatic field gradient is oriented transversally to the trajectory of the ions in the micro-reflectron.

3. The system of claim 2, wherein the micro-reflectron comprises at least two polarising electrodes of the resistive layer in contact with said regions of the resistive layer, said electrodes extending in the longitudinal direction of the micro-reflectron, in such a way as to generate in said resistive layer a potential gradient in the transverse direction of the micro-reflectron.

4. The system of claim 1, wherein the mass spectrometer is arranged in such a way that the trajectory of the ions in the mass spectrometer is included in a channel extending between two planes parallel to a main face of said at least one substrate, with the height of said channel being less than 1 mm and with the length of said channel being at least ten times greater than said height.

5. The system of claim 1, wherein said resistive layer of the micro-reflectron extends in a plane parallel to a main face of said at least one substrate.

6. The system of claim 1, wherein the beam of ions is emitted by the ion source in a direction orthogonal to the direction of introduction, in the spectrometer, of the gas coming from the separation module.

7. The system of claim 1, wherein the spectrometer comprises, between the source of ions and the micro-reflectron, a zone for accelerating the ions.

8. The system of claim 7, wherein the zone for accelerating the ions and the free-flight zone are arranged along a longitudinal wall of the micro-reflectron in such a way as to be adjacent.

9. The system of claim 8, wherein the micro-reflectron comprises a first opening that communicates with the acceleration zone for the inlet of the ions into the reflectron and a second opening that communicates with the free-flight zone for the outlet of the ions, said first and second openings being adjacent in the same wall of the micro-reflectron.

10. The system of claim 7, wherein the acceleration zone comprises two electrodes extending parallel to the direction of the beam of ions emitted by the ion source, said electrodes being able to be polarised in such a way as to generate an electrostatic field able to deviate the ions in a direction orthogonal to that of the ion beam at the outlet of the ion source in order to have said ions penetrate into the micro-reflectron.

11. The system of claim 10, wherein said electrodes of the acceleration zone are polarised by a pulse device, in such a way as to have the accelerated ions sequentially enter the micro-reflectron.

12. The system of claim 1, wherein the free-flight zone of the spectrometer is a zone that is separate from the micro-reflectron and that is devoid of any electrostatic field.

13. The system of claim 1, wherein the substrate in the volume of which said spectrometer is arranged is housed in a sealed case coupled to a vacuum pump in such a way as to apply a vacuum in said case.

14. The system of claim 1, wherein said at least one microcapillary chromatography column is arranged in the volume of at least one substrate.

15. The system of claim 14, wherein the separation module comprises at least one non-destructive micro or nano-detector in said at least one microcapillary chromatography column.

16. The system of claim 1, wherein the separation module comprises at least two microcapillary gas phase chromatography columns coupled in series and each one comprising a different stationary phase, and a flow modulator in order to regulate the flow of gas successively through each one of said columns.

17. The system of claim 14, wherein the separation module comprises at least two microcapillary gas phase chromatography columns coupled in series and each one comprising a different stationary phase, each one of said microcapillary columns comprising at least two non-destructive micro or nano-detectors arranged in said columns.

18. The system of claim 1, further comprising, upstream of the mass spectrometer, at least one non-destructive micro or nano-detector, said detector being arranged in a duct with a cross section equal to that of a microcapillary chromatography column to which it is connected in such a way as to not modify the cross section of passage of the gas.

19. The system of claim 18, wherein said spectrometer is arranged in the volume of a substrate, said substrate being housed in a sealed case coupled to a vacuum pump in such a way as to apply a vacuum in said case, wherein said non-destructive detector is an electromechanical nano-system comprising a resonator and wherein said detector is arranged in the vacuum pressurising case of the mass spectrometer.

20. The system of claim 1, further comprising, upstream of the separation module, a circuit for preconcentrating the gas to be analysed comprising a preconcentrator.

* * * * *